United States Patent
Inoue et al.

(10) Patent No.: US 9,508,941 B2
(45) Date of Patent: Nov. 29, 2016

(54) LIGHT-EMITTING ELEMENTS COMPRISING IRIDIUM ORGANOMETALLIC COMPLEXES COMPRISING ARYL-SUBSTITUTED PYRAZINES

(71) Applicant: Semiconductor Energy Laboratory Co., Ltd., Kanagawa-ken (JP)

(72) Inventors: Hideko Inoue, Kanagawa (JP); Tomoka Nakagawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 14/286,219

(22) Filed: May 23, 2014

(65) Prior Publication Data

US 2014/0256934 A1 Sep. 11, 2014

Related U.S. Application Data

(62) Division of application No. 13/333,218, filed on Dec. 21, 2011, now Pat. No. 8,735,581.

(30) Foreign Application Priority Data

Dec. 24, 2010 (JP) ................. 2010-287239

(51) Int. Cl.
*C07D 241/10* (2006.01)
*C01G 55/00* (2006.01)
*H01L 51/00* (2006.01)
*C07F 15/00* (2006.01)

(52) U.S. Cl.
CPC ....... *H01L 51/0085* (2013.01); *C07F 15/0033* (2013.01)

(58) Field of Classification Search
CPC .............................. C01G 55/00; C07D 241/10
USPC ........................................... 423/22; 544/336
See application file for complete search history.

(56) References Cited

U.S. PATENT DOCUMENTS

| 8,227,975 B2 | 7/2012 | Inoue et al. |
| 8,247,086 B2 | 8/2012 | Inoue et al. |
| 8,541,574 B2 | 9/2013 | Inoue et al. |
| 8,598,785 B2 | 12/2013 | Inoue et al. |
| 8,778,509 B2 | 7/2014 | Yasukawa et al. |
| 2005/0221123 A1 | 10/2005 | Inoue et al. |
| 2007/0129545 A1 | 6/2007 | Inoue et al. |
| 2008/0312437 A1 | 12/2008 | Inoue et al. |
| 2010/0145044 A1 | 6/2010 | Inoue et al. |
| 2012/0252762 A1 | 10/2012 | Oohara et al. |

FOREIGN PATENT DOCUMENTS

| JP | 2006-080419 A | 3/2006 |
| JP | 2007-161859 A | 6/2007 |
| JP | 2007-182429 A | 7/2007 |
| JP | 2009-013168 A | 1/2009 |
| JP | 2010-189376 A | 9/2010 |
| WO | WO 2007/029533 A1 | 3/2007 |
| WO | WO 2007/066556 A1 | 6/2007 |

OTHER PUBLICATIONS

Inoue, H. et al., "A Reaction of Singlet Oxygen with an Unsaturated Organic Molecule, 6.1.4, Quencher and Photosensitizer," Basic Chemistry Course Photochemistry I , Sep. 30, 1999, pp. 106-110, Maruzen.

Zhang, G. et al., "Synthesis and Luminescence Property of a New Yellow Phosphorescent Iridium (III) Pyrazine Complex," Chemical Journal of Chinese Universities, Mar. 1, 2004, vol. 25, No. 3, pp. 397-400.

*Primary Examiner* — Douglas M Willis
(74) *Attorney, Agent, or Firm* — Husch Blackwell LLP

(57) ABSTRACT

Provided is a novel organometallic complex which can be synthesized easily and emits phosphorescence, or a compound which emits red phosphorescence. The inventors focused on easy synthesis of an m-aminophenyl pyrazine derivative represented by the following general formula (G0), synthesized an organometallic complex having a structure in which the derivative is coordinated to a Group 9 or Group 10 metal ion, and further synthesized a useful substance which emits red phosphorescence.

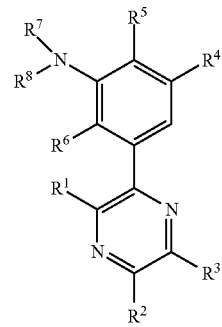

(G0)

20 Claims, 12 Drawing Sheets

LIGHT-EMITTING ELEMENTS COMPRISING IRIDIUM ORGANOMETALLIC COMPLEXES COMPRISING ARYL-SUBSTITUTED PYRAZINES

This application is a divisional of copending U.S. application Ser. No. 13/333,218, filed on Dec. 21, 2011 which is incorporated herein by reference.

BACKGROUND OF THE INVENTION

1. Field of the Invention

The present invention relates to an organometallic complex. In particular, the present invention relates to an organometallic complex that can convert a triplet excited state into luminescence.

2. Description of the Related Art

An organic compound absorbs light, thereby producing an excited state. Through this excited state, various reactions (photochemical reactions) occur in some cases, or luminescence is generated in some cases. Therefore, the organic compounds have been variously applied.

One example of the photochemical reactions is a reaction of singlet oxygen with an unsaturated organic molecule (oxygen addition) (see Non-Patent Document 1, for example). Since the ground state of oxygen molecules is a triplet state, oxygen molecules do not produce a singlet state (singlet oxygen) when they are excited directly by light. In contrast, when oxygen molecules interact with triplet excited molecules other than oxygen, the oxygen molecules form singlet oxygen, resulting in an oxygen addition reaction. Here, the compound that forms the triplet excited molecules by light and enables formation of singlet oxygen is called a photosensitizer.

Thus, formation of singlet oxygen requires a photosensitizer that can form triplet excited molecules by light excitation. However, it is unlikely that a typical organic compound is converted to a triplet excited molecule because the ground state of the organic compound is typically a singlet state and photoexcitation to a triplet excited state is forbidden transition. For such a photosensitizer, a compound that can easily undergo intersystem crossing from the singlet excited state to the triplet excited state (or a compound that allows forbidden transition in which the compound is directly converted to a triplet excited state by photoexcitation) is thus needed. That is, such a compound can be used as a photosensitizer and regarded as being useful.

Furthermore, the above compound often emits phosphorescence. Phosphorescence refers to luminescence generated by transition between energies of different multiplicity. In an ordinary organic compound, phosphorescence refers to luminescence that is generated at the time of relax from a triplet excited state to a singlet ground state (in contrast, fluorescence refers to luminescence that is generated at the time of relax from a singlet excited state to a singlet ground state). Application fields of compounds that are capable of emitting phosphorescence, in other words, compounds that are capable of converting a triplet excited state into luminescence (hereinafter, referred to as a phosphorescent compound), include a light-emitting element containing an organic compound as a light-emitting substance.

An example of a structure of such a light-emitting element is a simple structure in which a light-emitting layer containing an organic compound that is a light-emitting substance is merely provided between electrodes. Light-emitting elements having such a structure can achieve thinness, light-weight, high-speed response to signals, low-voltage DC drive, and the like. Therefore, attention has been directed to the light-emitting elements as next-generation flat panel display elements. Further, a display including this light-emitting element is superior in contrast, image quality, and wide viewing angle.

The light-emitting mechanism of the light-emitting elements in which organic compounds are used as the light-emitting substance is carrier injection. That is, by applying a voltage with a light-emitting layer interposed between electrodes, electrons and holes injected from the electrodes recombine to make the light-emitting substance excited, and light is emitted when the excited state relaxes to a ground state. As in the case of the photoexcitation, types of the excited state of organic compounds include a singlet excited state ($S^*$) and a triplet excited state ($T^*$). In addition, the statistical generation ratio thereof in a light-emitting element is considered to be $S^*:T^*=1:3$.

At room temperature, a compound that converts a singlet excited state into luminance (hereinafter, referred to as a fluorescent compound) emits light only from the singlet excited state (fluorescence), and does not emit light from the triplet excited state (phosphorescence). Accordingly, the internal quantum efficiency (the ratio of generated photons to injected carriers) in a light-emitting element formed using a fluorescent compound is assumed to have a theoretical limit of 25% based on $S^*:T^*=1:3$.

On the other hand, with a light-emitting element formed using a compound that converts a triplet excited state into luminance (hereinafter, referred to as a phosphorescent compound), the internal quantum efficiency can be improved to 100% in theory; namely, the emission efficiency can be 4 times as high as that of a light-emitting element formed using a fluorescent compound. Therefore, the light-emitting element formed using a phosphorescent compound has been actively developed in recent years in order to achieve a highly efficient light-emitting element (see Non-Patent Document 2, for example). An organometallic complex that contains iridium or the like as a central metal is particularly attracting attention as a phosphorescent compound because of its high phosphorescence quantum efficiency.

REFERENCE

Non-Patent Document

[Non-Patent Document 1]
Inoue, Haruo, and three others, *Basic Chemistry Course PHOTOCHEMISTRY I*, pp. 106-110, Maruzen Co., Ltd.
[Non-Patent Document 2]
Zhang, Guo-Lin, and five others, *Gaodeng Xuexiao Huaxue Xuebao* [*Chemical Journal of Chinese Universities*] (2004), vol. 25, No. 3, pp. 397-400.

SUMMARY OF THE INVENTION

An object of one embodiment of the present invention is to provide a novel organometallic complex which can be synthesized easily and emits phosphorescence. Another object of one embodiment of the present invention is to provide a compound which emits red phosphorescence.

The inventors focused on easy synthesis of an m-aminophenyl pyrazine derivative represented by the following general formula (G0). The inventors synthesized an organometallic complex having a structure in which the derivative is coordinated to a Group 9 or Group 10 metal ion, and further synthesized a useful substance which emits red phosphorescence.

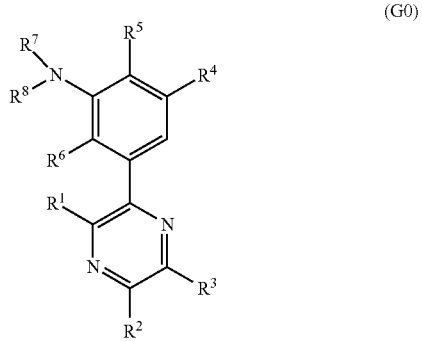

(G0)

Note that in the general formula (G0), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ and $R^3$ separately represent hydrogen or an alkyl group having 1 to 4 carbon atoms. Furthermore, $R^4$ to $R^6$ separately represent any of hydrogen, an alkyl group having 1 to 4 carbon atoms, an alkoxy group having 1 to 4 carbon atoms, a halogen group, a trifluoromethyl group, and an aryl group having 6 to 12 carbon atoms. Further, $R^7$ and $R^8$ separately represent an alkyl group having 1 to 4 carbon atoms or an aryl group having 6 to 12 carbon atoms. In addition, $R^7$ and $R^8$ may be bonded to each other through a carbon atom, an oxygen atom, a sulfur atom, or a nitrogen atom having a substituent, to form a substituted or unsubstituted five-membered ring or a substituted or unsubstituted six-membered ring.

Therefore, one embodiment of the present invention is an organometallic complex which is represented by the following general formula (G1) and has a structure in which an m-aminophenyl pyrazine derivative is coordinated to a Group 9 or Group 10 metal ion.

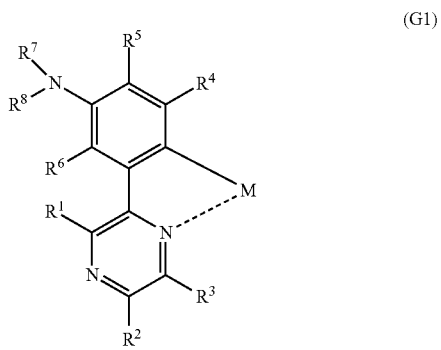

(G1)

Note that in the general formula (G1), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ and $R^3$ separately represent hydrogen or an alkyl group having 1 to 4 carbon atoms. Furthermore, $R^4$ to $R^6$ separately represent any of hydrogen, an alkyl group having 1 to 4 carbon atoms, an alkoxy group having 1 to 4 carbon atoms, a halogen group, a trifluoromethyl group, and an aryl group having 6 to 12 carbon atoms. Further, $R^7$ and $R^8$ separately represent an alkyl group having 1 to 4 carbon atoms or an aryl group having 6 to 12 carbon atoms. In addition, $R^7$ and $R^8$ may be bonded to each other through a carbon atom, an oxygen atom, a sulfur atom, or a nitrogen atom having a substituent, to form a substituted or unsubstituted five-membered ring or a substituted or unsubstituted six-membered ring. Further, M is a central metal and represents a Group 9 element or a Group 10 element.

An organometallic complex having the above structure is a compound which emits red phosphorescence. In addition, the organometallic complex has a low molecular weight, and high thermal stability and sublimation property, and thus can be easily evaporated in fabrication of an element. In general, it is necessary to extend the π-conjugation of a light-emitting material in order to obtain red light emission with high color purity, so that the molecular weight of the organometallic complex increases. As a result, the sublimation temperature of the organometallic complex becomes higher, and thus evaporation of the organometallic complex becomes difficult and the organometallic complex becomes likely to decompose while being evaporated. On the other hand, an organometallic complex according to one embodiment of the present invention can provide red light emission with high color purity and has a small molecular weight, so that the above problems do not arise.

An organometallic complex of an m-aminophenyl pyrazine derivative in which an amino group is bonded at a meta position can emit red light with high color purity as compared to an organometallic complex of an aminophenyl pyrazine derivative in which an amino group is bonded at an ortho position or a para position. In addition, the organometallic complex of an m-aminophenyl pyrazine derivative in which an amino group is bonded at a meta position has a reduced steric hindrance in the molecule and high stability of the molecule, and thus reliability of the element is increased, as compared to the organometallic complex of an aminophenyl pyrazine derivative in which an amino group is bonded at an ortho position or a para position.

Another embodiment of the present invention is an organometallic complex which is represented by the following general formula (G2) and has a structure in which an m-aminophenyl pyrazine derivative is coordinated to a Group 9 or Group 10 metal ion.

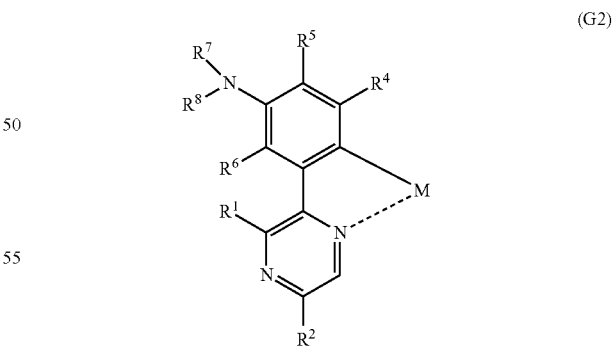

(G2)

Note that in the general formula (G2), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, $R^4$ to $R^6$ separately represent any of hydrogen, an alkyl group having 1 to 4 carbon atoms, an alkoxy group having 1 to 4 carbon atoms, a halogen group, a trifluoromethyl group, and an aryl group having 6 to 12 carbon atoms. Further, $R^7$ and $R^8$ separately represent an alkyl group having 1 to 4 carbon atoms or an aryl group having 6 to 12 carbon atoms. In addition, $R^7$ and $R^8$ may be bonded to each other through a carbon atom, an oxygen atom, a sulfur atom, or a nitrogen atom having a substituent, to form a substituted or unsubstituted five-membered ring or a substituted or unsubstituted six-membered ring. Further, M is a central metal and represents a Group 9 element or a Group 10 element.

An organometallic complex having the above structure is synthesized in a dramatically high yield because generation of an impurity and decomposition of the objective substance are suppressed in the synthesis reaction.

Another embodiment of the present invention is an organometallic complex which is represented by the following general formula (G3) and has a structure in which an m-aminophenyl pyrazine derivative is coordinated to a Group 9 or Group 10 metal ion.

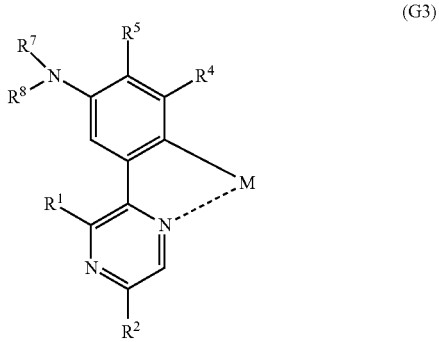

(G3)

Note that in the general formula (G3), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, $R^4$ and $R^5$ separately represent any of hydrogen, an alkyl group having 1 to 4 carbon atoms, an alkoxy group having 1 to 4 carbon atoms, a halogen group, a trifluoromethyl group, and an aryl group having 6 to 12 carbon atoms. Further, $R^7$ and $R^8$ separately represent an alkyl group having 1 to 4 carbon atoms or an aryl group having 6 to 12 carbon atoms. In addition, $R^7$ and $R^8$ may be bonded to each other through a carbon atom, an oxygen atom, a sulfur atom, or a nitrogen atom having a substituent, to form a substituted or unsubstituted five-membered ring or a substituted or unsubstituted six-membered ring. Further, M is a central metal and represents a Group 9 element or a Group 10 element.

An organometallic complex having the above structure is preferable because the organometallic complex emits red phosphorescence and the ligand is synthesized easily.

Another embodiment of the present invention is an organometallic complex having a structure represented by the following general formula (G4).

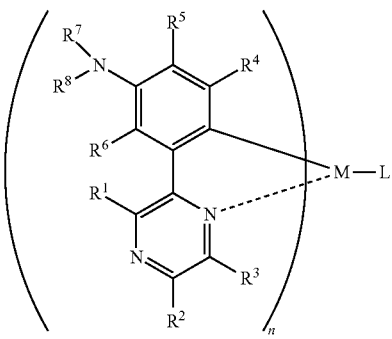

(G4)

Note that in the general formula (G4), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ and $R^3$ separately represent hydrogen or an alkyl group having 1 to 4 carbon atoms. Furthermore, $R^4$ to $R^6$ separately represent any of hydrogen, an alkyl group having 1 to 4 carbon atoms, an alkoxy group having 1 to 4 carbon atoms, a halogen group, a trifluoromethyl group, and an aryl group having 6 to 12 carbon atoms. Further, $R^7$ and $R^8$ separately represent an alkyl group having 1 to 4 carbon atoms or an aryl group having 6 to 12 carbon atoms. In addition, $R^7$ and $R^8$ may be bonded to each other through a carbon atom, an oxygen atom, a sulfur atom, or a nitrogen atom having a substituent, to form a substituted or unsubstituted five-membered ring or a substituted or unsubstituted six-membered ring. Further, M is a central metal and represents a Group 9 element or a Group 10 element. L represents a monoanionic ligand. Moreover, n is 2 when the central metal is a Group 9 element, and n is 1 when the central metal is a Group 10 element.

The above organometallic complex is a specific example of the organometallic complex which is represented by the following general formula (G1) and has a structure in which an m-aminophenyl pyrazine derivative is coordinated to a Group 9 or Group 10 metal ion, and is a compound which emits red phosphorescence. In addition, the organometallic complex has a low molecular weight, and high thermal stability and sublimation property, and thus can be easily evaporated in fabrication of an element.

An organometallic complex of an m-aminophenyl pyrazine derivative in which an amino group is bonded at a meta position can emit red light with high color purity (as compared to an organometallic complex of an aminophenyl pyrazine derivative in which an amino group is bonded at an ortho position or a para position). In addition, the organometallic complex of an m-aminophenyl pyrazine derivative in which an amino group is bonded at a meta position has a reduced steric hindrance in the molecule and high stability of the molecule, and thus reliability of the element is increased (as compared to the organometallic complex of an aminophenyl pyrazine derivative in which an amino group is bonded at an ortho position or a para position).

Another embodiment of the present invention is an organometallic complex having a structure represented by the following general formula (G5).

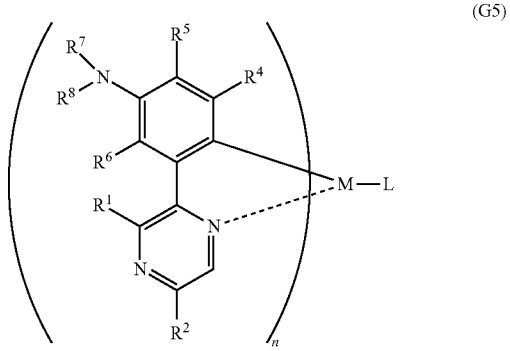

(G5)

Note that in the general formula (G5), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, $R^4$ to $R^6$ separately represent any of hydrogen, an alkyl group having 1 to 4 carbon atoms, an alkoxy group having 1 to 4 carbon atoms, a halogen group, a trifluoromethyl group, and an aryl group having 6 to 12 carbon atoms. Further, $R^7$ and $R^8$ separately represent an alkyl group having 1 to 4 carbon atoms or an aryl group having 6 to 12 carbon atoms. In addition, $R^7$ and $R^8$ may be bonded to each other through a carbon atom, an oxygen atom, a sulfur atom, or a nitrogen atom having a substituent, to form a substituted or unsubstituted five-membered ring or a substituted or unsubstituted six-membered ring. Further, M is a central metal and represents a Group 9 element or a Group 10 element. L represents a monoanionic ligand. Moreover, n is 2 when the central metal is a Group 9 element, and n is 1 when the central metal is a Group 10 element.

The above organometallic complex is a specific example of the organometallic complex which is represented by the general formula (G2) and has a structure in which an m-aminophenyl pyrazine derivative is coordinated to a Group 9 or Group 10 metal ion. The organometallic complex emits red phosphorescence and the ligand is synthesized easily. In addition, the yield is dramatically increased because generation of an impurity and decomposition of the objective substance are suppressed in the synthesis reaction.

Another embodiment of the present invention is an organometallic complex having a structure represented by the following general formula (G6).

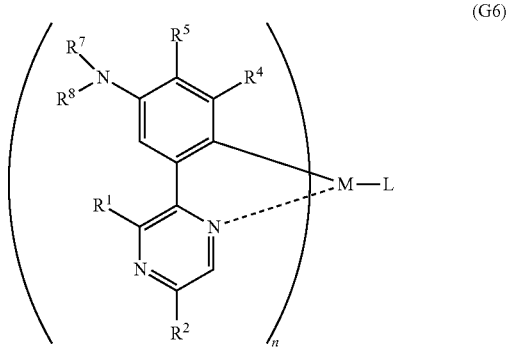

(G6)

Note that in the general formula (G6), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, $R^4$ and $R^5$ separately represent any of hydrogen, an alkyl group having 1 to 4 carbon atoms, an alkoxy group having 1 to 4 carbon atoms, a halogen group, a trifluoromethyl group, and an aryl group having 6 to 12 carbon atoms. Further, $R^7$ and $R^8$ separately represent an alkyl group having 1 to 4 carbon atoms or an aryl group having 6 to 12 carbon atoms. In addition, $R^7$ and $R^8$ may be bonded to each other through a carbon atom, an oxygen atom, a sulfur atom, or a nitrogen atom having a substituent, to form a substituted or unsubstituted five-membered ring or a substituted or unsubstituted six-membered ring. Further, M is a central metal and represents a Group 9 element or a Group 10 element. L represents a monoanionic ligand. Moreover, n is 2 when the central metal is a Group 9 element, and n is 1 when the central metal is a Group 10 element.

The above organometallic complex is a specific example of the organometallic complex which is represented by the general formula (G3) and has a structure in which an m-aminophenyl pyrazine derivative is coordinated to a Group 9 or Group 10 metal ion. The organometallic complex is preferable because the organometallic complex emits red phosphorescence and the ligand is synthesized easily.

Another embodiment of the present invention is an organometallic complex in which the monoanionic ligand according to the general formula (G4), the general formula (G5), or the general formula (G6) is any of the following: a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen.

The above organometallic complex is a specific example of the organometallic complex which is represented by the general formula (G4), the general formula (G5), or the general formula (G6), and is a compound which emits red phosphorescence. In addition, the organometallic complex has a low molecular weight, and high thermal stability and sublimation property, and thus can be easily evaporated in fabrication of an element.

An organometallic complex of an m-aminophenyl pyrazine derivative in which an amino group is bonded at a meta position can emit red light with high color purity as compared to an organometallic complex of an aminophenyl pyrazine derivative in which an amino group is bonded at an ortho position or a para position. In addition, the organometallic complex of an m-aminophenyl pyrazine derivative in which an amino group is bonded at a meta position has a reduced steric hindrance in the molecule and high stability of the molecule, and thus reliability of the element is increased as compared to the organometallic complex of an aminophenyl pyrazine derivative in which an amino group is bonded at an ortho position or a para position.

Another embodiment of the present invention is an organometallic complex in which the monoanionic ligand according to the general formula (G4), the general formula (G5), or the general formula (G6) includes any of the following structural formulas (L1) to (L8).

(L1) 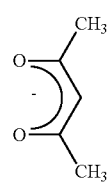

(L2) 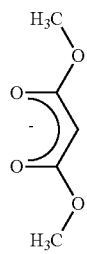

(L3) 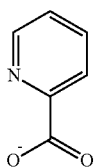

(L4) 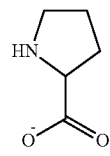

(L5) 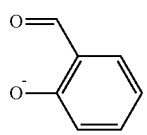

(L6) 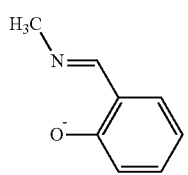

(L7) 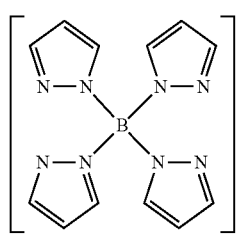

(L8) 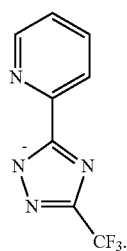

Any of the ligands has high coordinative ability and can be obtained at a low cost. Therefore, the organometallic complex is stable, and the organometallic complex can be provided at a low cost.

Another embodiment of the present invention is an organometallic complex having a structure represented by the following general formula (G7).

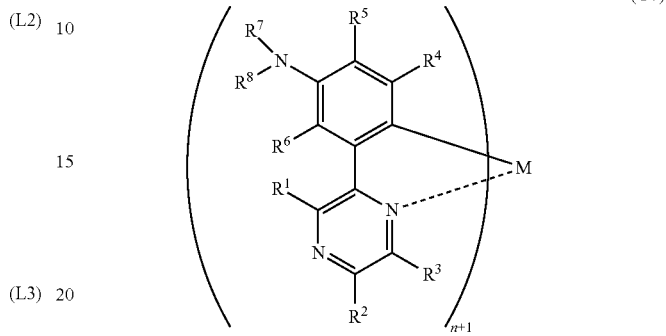

(G7)

Note that in the general formula (G7), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ and $R^3$ separately represent hydrogen or an alkyl group having 1 to 4 carbon atoms. Furthermore, $R^4$ to $R^6$ separately represent any of hydrogen, an alkyl group having 1 to 4 carbon atoms, an alkoxy group having 1 to 4 carbon atoms, a halogen group, a trifluoromethyl group, and an aryl group having 6 to 12 carbon atoms. Further, $R^7$ and $R^8$ separately represent an alkyl group having 1 to 4 carbon atoms or an aryl group having 6 to 12 carbon atoms. In addition, $R^7$ and $R^8$ may be bonded to each other through a carbon atom, an oxygen atom, a sulfur atom, or a nitrogen atom having a substituent, to form a substituted or unsubstituted five-membered ring or a substituted or unsubstituted six-membered ring. Further, M is a central metal and represents a Group 9 element or a Group 10 element. Moreover, n is 2 when the central metal is a Group 9 element, and n is 1 when the central metal is a Group 10 element.

An organometallic complex having the structure represented by the general formula (G7) is an organometallic complex in which only the same m-aminophenyl pyrazine derivatives are coordinated to a Group 9 or Group 10 metal ion in the organometallic complex represented by the general formula (G4). Such a structure is preferable for higher heat resistance and higher reliability of the element.

Another embodiment of the present invention is an organometallic complex having a structure represented by the following general formula (G8).

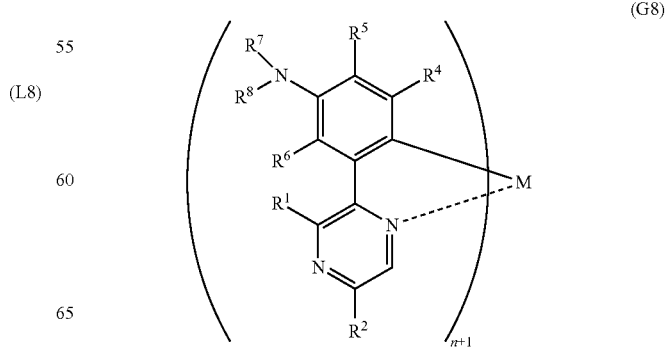

(G8)

Note that in the general formula (G8), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, $R^4$ to $R^6$ separately represent any of hydrogen, an alkyl group having 1 to 4 carbon atoms, an alkoxy group having 1 to 4 carbon atoms, a halogen group, a trifluoromethyl group, and an aryl group having 6 to 12 carbon atoms. Further, $R^7$ and $R^8$ separately represent an alkyl group having 1 to 4 carbon atoms or an aryl group having 6 to 12 carbon atoms. In addition, $R^7$ and $R^8$ may be bonded to each other through a carbon atom, an oxygen atom, a sulfur atom, or a nitrogen atom having a substituent, to form a substituted or unsubstituted five-membered ring or a substituted or unsubstituted six-membered ring. Further, M is a central metal and represents a Group 9 element or a Group 10 element. Moreover, n is 2 when the central metal is a Group 9 element, and n is 1 when the central metal is a Group 10 element.

An organometallic complex having the structure represented by the general formula (G8) is an organometallic complex in which only the same m-aminophenyl pyrazine derivatives are coordinated to a Group 9 or Group 10 metal ion in the organometallic complex represented by the general formula (G5). Such a structure is preferable because generation of an impurity and decomposition of the objective substance are suppressed in the synthesis reaction; and thus the synthesis yield is dramatically increased.

Another embodiment of the present invention is an organometallic complex having a structure represented by the following general formula (G9).

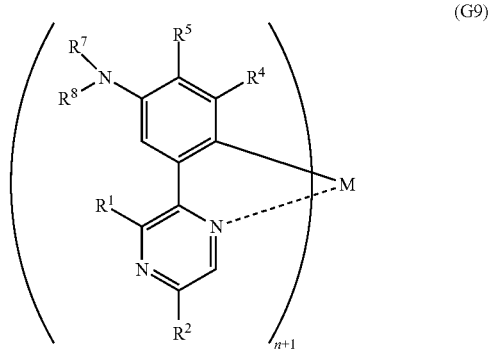

(G9)

Note that in the general formula (G9), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, $R^4$ and $R^5$ separately represent any of hydrogen, an alkyl group having 1 to 4 carbon atoms, an alkoxy group having 1 to 4 carbon atoms, a halogen group, a trifluoromethyl group, and an aryl group having 6 to 12 carbon atoms. Further, $R^7$ and $R^8$ separately represent an alkyl group having 1 to 4 carbon atoms or an aryl group having 6 to 12 carbon atoms. In addition, $R^7$ and $R^8$ may be bonded to each other through a carbon atom, an oxygen atom, a sulfur atom, or a nitrogen atom having a substituent, to form a substituted or unsubstituted five-membered ring or a substituted or unsubstituted six-membered ring. Further, M is a central metal and represents a Group 9 element or a Group 10 element. Moreover, n is 2 when the central metal is a Group 9 element, and n is 1 when the central metal is a Group 10 element.

An organometallic complex having the structure represented by the general formula (G9) is an organometallic complex in which only the same m-aminophenyl pyrazine derivatives are coordinated to a Group 9 or Group 10 metal ion in the organometallic complex represented by the general formula (G6). Such a structure is preferable because the organometallic complex emits red phosphorescence and the ligand is synthesized easily.

Another embodiment of the present invention is an organometallic complex in which the central metal M is iridium or platinum in any of the above-described organometallic complexes.

The above organometallic complex including iridium or platinum as the central metal M emits phosphorescence efficiently. This is because iridium or platinum provides a prominent heavy atom effect.

Another embodiment of the present invention is a light-emitting element including any of the above organometallic complexes. The organometallic complex can convert triplet excitation energy into red light emission. Therefore, the organometallic complex has an effect of increasing the emission efficiency of the light-emitting element.

Another embodiment of the present invention is a light-emitting element including any of the above organometallic complexes as a light-emitting substance. Since the organometallic complex emits phosphorescence, the use of the organometallic complex as a light-emitting substance has an effect of increasing the efficiency of the light-emitting element.

Another embodiment of the present invention is a light-emitting device including any of the above light-emitting elements. Application of the high-efficiency light-emitting element including the fluorescent organometallic complex can reduce the power consumption of the light-emitting device.

One embodiment of the present invention includes, in its category, an electronic device including the light-emitting device. Application of the high-efficiency light-emitting device including the phosphorescent organometallic complex can reduce the power consumption of the electronic device.

Note that the light-emitting device in this specification refers to an image display device, a light-emitting device, or a light source (including a lighting device). Further, the light-emitting device includes any of the following modules in its category: a module in which a connector such as a flexible printed circuit (FPC), a tape automated bonding (TAB) tape, or a tape carrier package (TCP) is attached to a light-emitting device; a module having a TAB tape or a TCP provided with a printed wiring board at the end thereof; and a module having an integrated circuit (IC) directly mounted over a light-emitting device by a chip on glass (COG) method.

One embodiment of the present invention provides a novel phosphorescent organometallic complex.

Another embodiment of the present invention provides an organometallic complex which emits red phosphorescence.

Another embodiment of the present invention provides a light-emitting element which emits red phosphorescence.

Another embodiment of the present invention provides a light-emitting device.

Another embodiment of the present invention provides an electronic device.

DETAILED DESCRIPTION OF THE INVENTION

Figure 1:
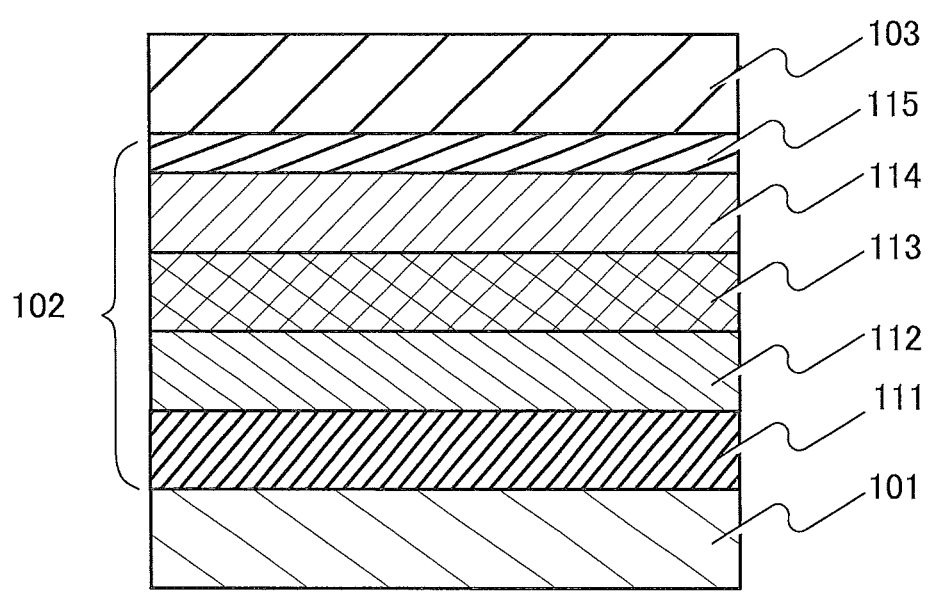
FIG. 1 is a view illustrating a light-emitting element according to one embodiment of the present invention.

Hereinafter, Embodiments of the present invention will be described in detail with reference to the drawings. However, the present invention is not limited to the following description, and the mode and details can be variously changed unless departing from the scope and spirit of the invention. Therefore, the invention should not be construed as being limited to the description in the following embodiments.

Embodiment 1

Embodiment 1 shows organometallic complexes which are embodiments of the present invention and methods for synthesis thereof. Specifically, description is given of methods of synthesizing an m-aminophenyl pyrazine derivative and an organometallic complex having a structure in which the m-aminophenyl pyrazine derivative is coordinated to a Group 9 or Group 10 metal ion.

[Method of Synthesizing m-Aminophenyl Pyrazine Derivative Represented by General Formula (G0)]

The m-aminophenyl pyrazine derivative represented by the following general formula (G0) can be synthesized by any of the following simple synthesis schemes (a), (a'), and (a"). Note that in each of the synthesis schemes (a), (a'), and (a"), X represents a halogen.

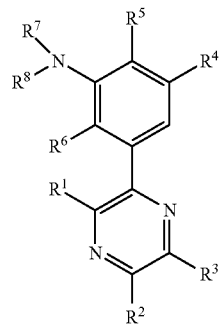

(G0)

In the general formula (G0), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ and $R^3$ separately represent hydrogen or an alkyl group having 1 to 4 carbon atoms. Furthermore, $R^4$ to $R^6$ separately represent any of hydrogen, an alkyl group having 1 to 4 carbon atoms, an alkoxy group having 1 to 4 carbon atoms, a halogen group, a trifluoromethyl group, and an aryl group having 6 to 12 carbon atoms. Further, $R^7$ and $R^8$ separately represent an alkyl group having 1 to 4 carbon atoms or an aryl group having 6 to 12 carbon atoms. In addition, $R^7$ and $R^8$ may be bonded to each other through a carbon atom, an oxygen atom, a sulfur atom, or a nitrogen atom having a substituent, to form a substituted or unsubstituted five-membered ring or a substituted or unsubstituted six-membered ring.

As shown in the following scheme (a) for example, the m-aminophenyl pyrazine derivative can be obtained by a reaction between a lithium compound of m-alkoxyaryl or a Grignard reagent of m-alkoxyaryl shown as (A1) and a pyrazine compound (A2).

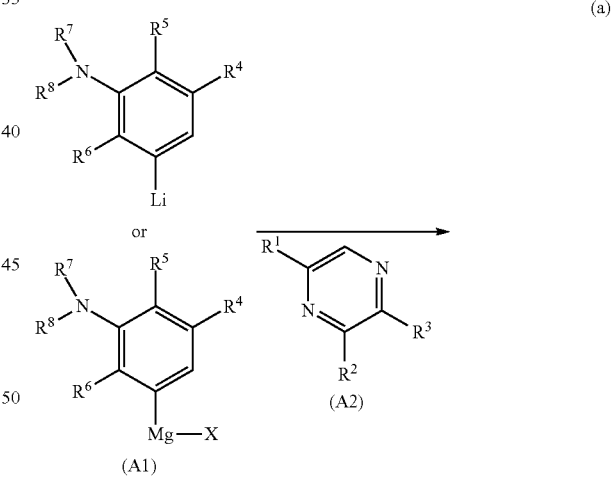

(a)

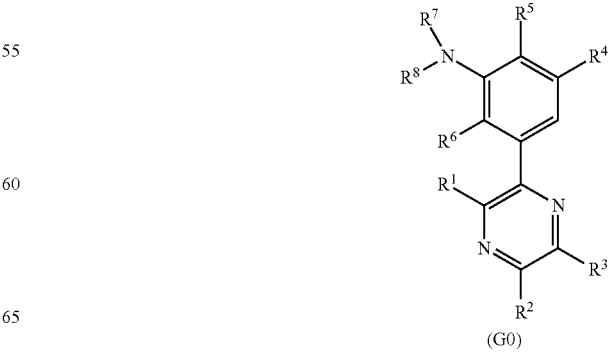

(G0)

Alternatively, as shown in the following scheme (a'), the m-aminophenyl pyrazine derivative can be obtained by coupling of m-alkoxyphenyl boronic acid (A1') and a halogenated pyrazine compound (A2').

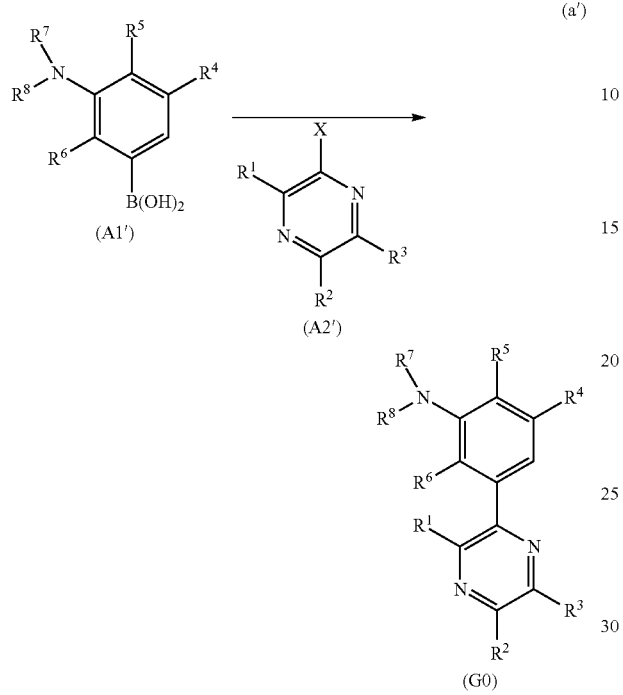

Further alternatively, as shown in the following scheme (a''), the m-aminophenyl pyrazine derivative can be obtained by a reaction between diketone of m-alkoxyaryl (A1'') and diamine (A2'').

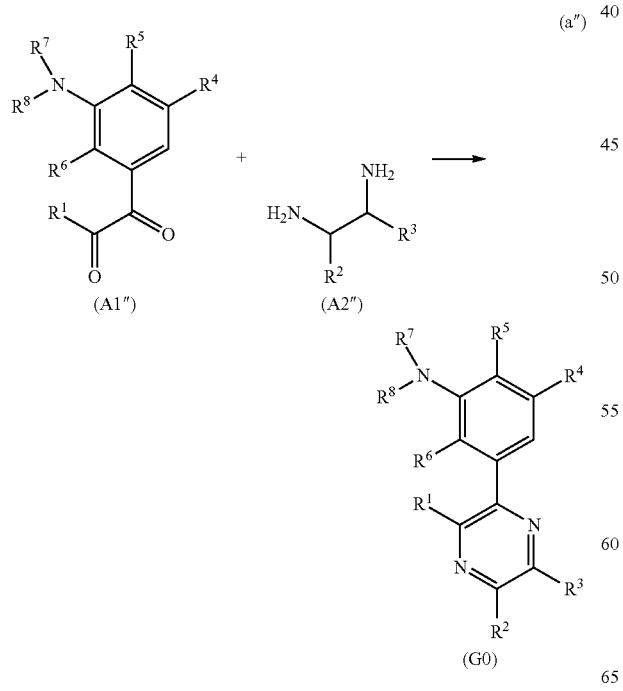

Various types of the above-described compounds (A1), (A2), (A1'), (A2'), (A1''), and (A2'') are commercially available or can be synthesized. Accordingly, it is possible to synthesize many types of the m-alkoxyphenyl pyrazine derivative represented by the general formula (G0). Therefore, features of the organometallic complex according to one embodiment of the present invention include a wide variety of ligands thereof, effects of emitting phosphorescence, and potential contribution to various light-emitting properties.

[Method of Synthesizing Organometallic Complex, One Embodiment of the Present Invention Represented by General Formula (G4)]

Next, description is given of methods of synthesizing an organometallic complex which is formed by orthometalation of an m-aminophenyl pyrazine derivative represented by the general formula (G0), i.e., an organometallic complex represented by the following general formula (G1). Specifically, the description includes a method of synthesizing an organometallic complex represented by the following general formula (G4) and a method of synthesizing an organometallic complex represented by the following general formula (G7).

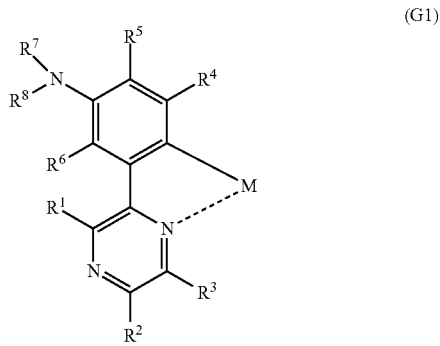

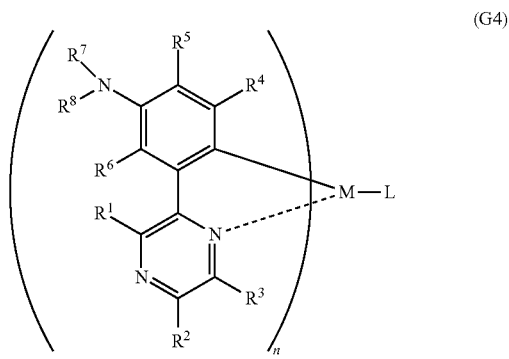

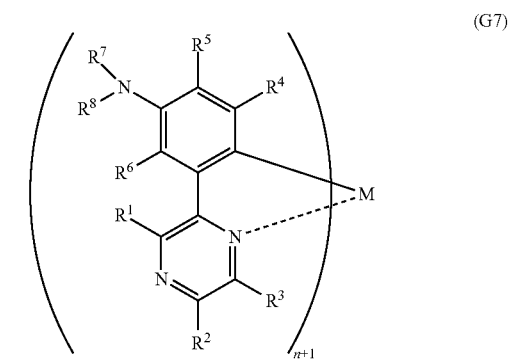

In the general formulas (G1), (G4), and (G7), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ and $R^3$ separately represent hydrogen or an alkyl group having 1 to 4 carbon atoms. Furthermore, $R^4$ to $R^6$ separately represent any of hydrogen, an alkyl group having 1 to 4 carbon atoms, an alkoxy group having 1 to 4 carbon atoms, a halogen group, a trifluoromethyl group, and an aryl group having 6 to 12 carbon atoms. Further, $R^7$ and $R^8$ separately represent an alkyl group having 1 to 4 carbon atoms or an aryl group having 6 to 12 carbon atoms. In addition, $R^7$ and $R^8$ may be bonded to each other through a carbon atom, an oxygen atom, a sulfur atom, or a nitrogen atom having a substituent, to form a substituted or unsubstituted five-membered ring or a substituted or unsubstituted six-membered ring. Further, M is a central metal and represents a Group 9 element or a Group 10 element. In the general formulas (G4) and (G7), n is 2 when the central metal is a Group 9 element, and n is 1 when the central metal is a Group 10 element. In the general formula (G4), L represents a monoanionic ligand.

First, as shown in the following synthesis scheme (b), the m-aminophenyl pyrazine derivative represented by the general formula (G0) and a compound of a metal belonging to Group 9 or Group 10 which contains a halogen (a metal halide or a metal complex) are heated with an alcohol-based solvent (e.g., glycerol, ethyleneglycol, 2-methoxyethanol, or 2-ethoxyethanol) alone or with a mixed solvent of water and one or more kinds of the above alcohol-based solvents, thereby obtaining a binuclear complex (B), which is a type of organometallic complexes having the structure represented by the general formula (G1).

Examples of the Group 9 or Group 10 metal compound containing a halogen include rhodium chloride hydrate, palladium chloride, iridium chloride hydrate, iridium chloride hydrochloride hydrate, potassium tetrachloroplatinate (II), and the like, but are not limited to these examples. Note that in the synthesis scheme (b), M represents a Group 9 element or a Group 10 element, and X represents a halogen. Moreover, n is 2 when M is a Group 9 element, and n is 1 when M is a Group 10 element.

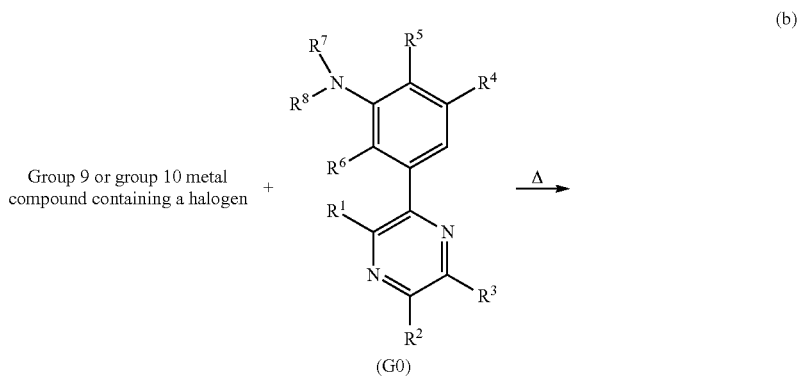

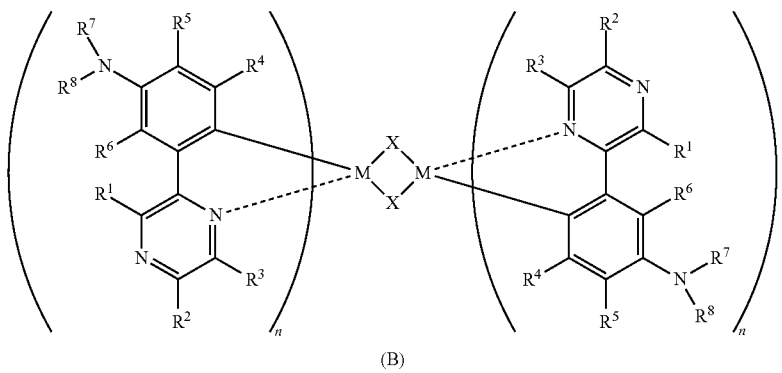

Next, the binuclear organometallic complex (B) is reacted with a material HL of a monoanionic ligand, thereby obtaining the organometallic complex represented by the general formula (G4) (synthesis scheme (c)). Note that in the synthesis scheme (c), M represents a Group 9 element or a Group 10 element, and X represents a halogen. Moreover, n is 2 when M is a Group 9 element, and n is 1 when M is a Group 10 element.

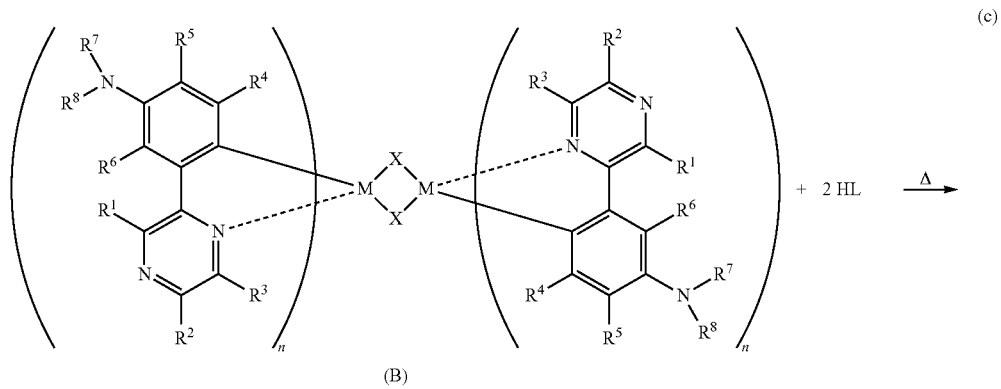

(B)

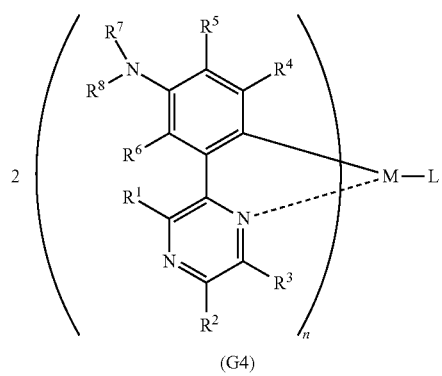

(G4)

Examples of the monoanionic ligand (L) in the general formula (G4) include a monoanionic bidentate chelate ligand having a b-diketone structure, a monoanionic bidentate chelate ligand having a carboxyl group, a monoanionic bidentate chelate ligand having a phenolic hydroxyl group, or a monoanionic bidentate chelate ligand in which two ligand elements are both nitrogen.

Further, the monoanionic ligand (L) in the general formula (G4) can be any of the following structural formulas (L1) to (L8).

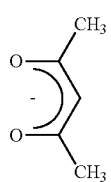

(L1)

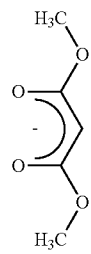

(L2)

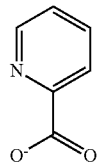

(L3)

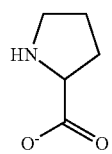

(L4)

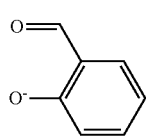

(L5)

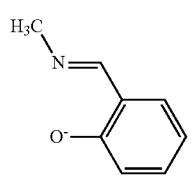

(L6)

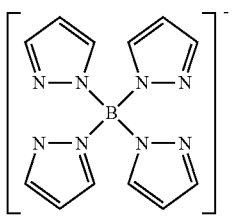

(L7)

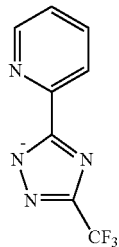

(L8)

The organometallic complex represented by the above general formula (G7) can be synthesized by the following synthesis scheme (d). In other words, the organometallic complex represented by the general formula (G7) can be obtained by heating the organometallic complex represented by the general formula (G4) and the m-aminophenyl pyrazine derivative represented by the general formula (G0) in a high boiling solvent such as glycerin at a high temperature of about 200° C. Note that in the synthesis scheme (d), M represents a Group 9 element or a Group 10 element, and X represents a halogen. Moreover, n is 2 when M is a Group 9 element, and n is 1 when M is a Group 10 element.

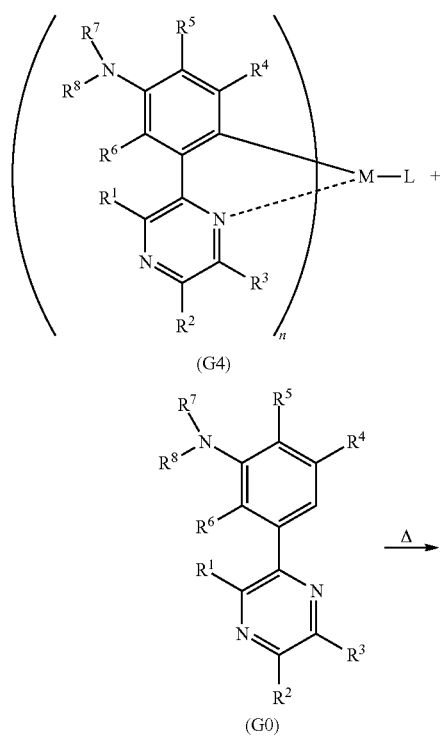

(d)

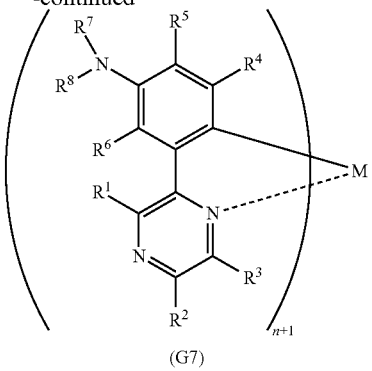

(G7)

Examples of the synthesis methods are described above, but methods of synthesizing the organometallic complex according to one embodiment of the present invention are not limited thereto.

The organometallic complex according to one embodiment of the present invention can be combined with any of a variety of central metals M and monoanionic ligands L as appropriate to form a variety of organometallic complexes. Specifically, the organometallic complex according to one embodiment of the present invention is represented by any of the following structural formulas (the following structural formulas (100) to (147)). Note that the present invention is not limited to these structural formulas.

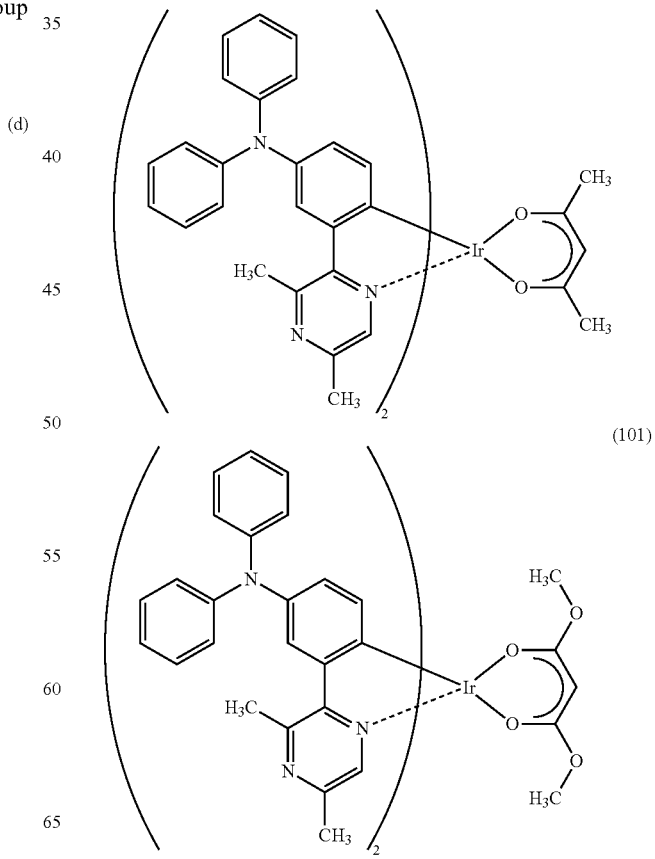

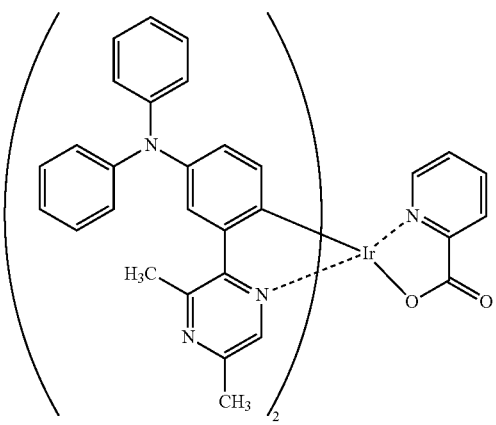
(102)
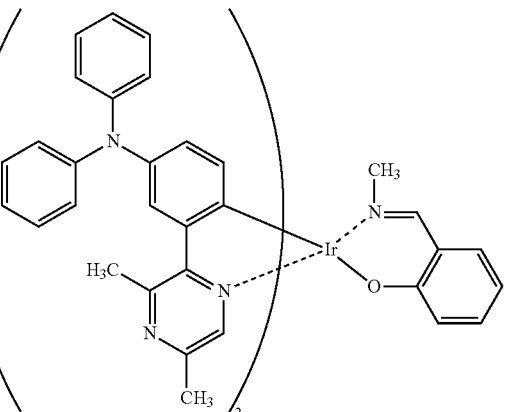
(105)
(103)
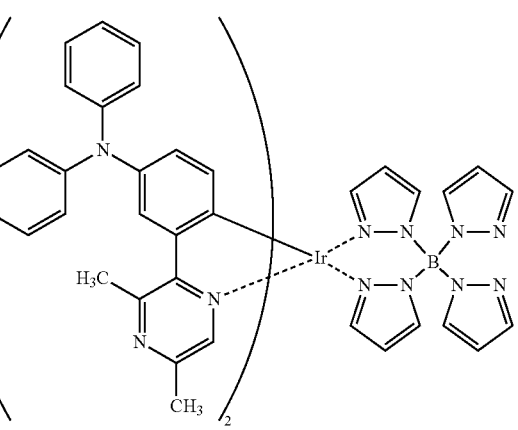
(106)
(104)
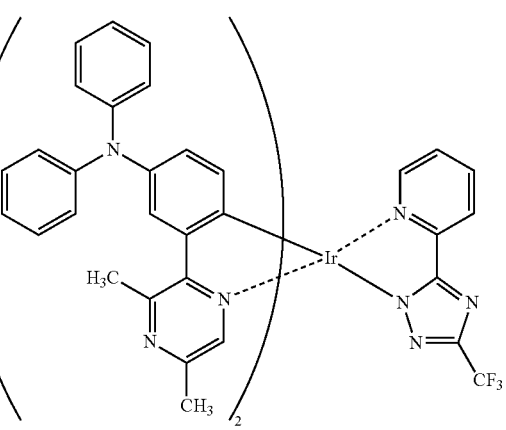
(107)

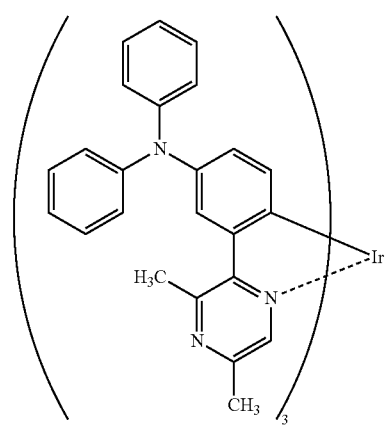
(108)
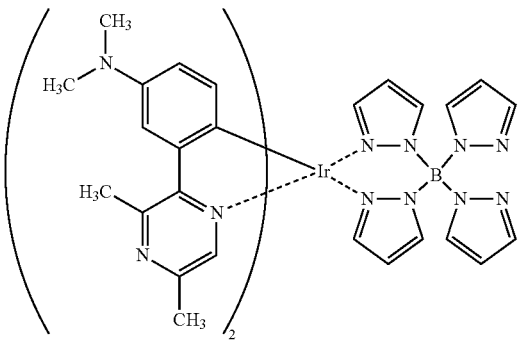
(112)
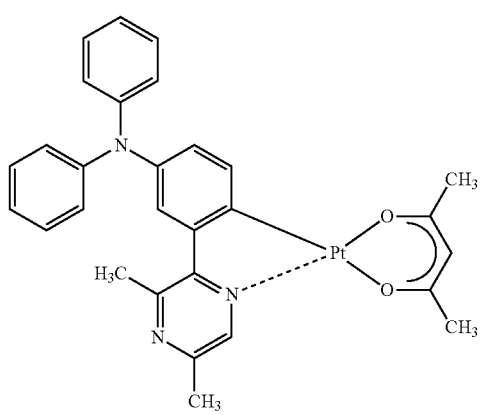
(109)
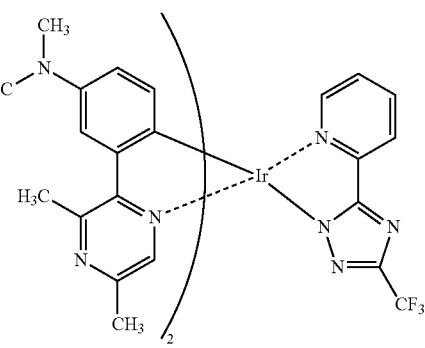
(113)
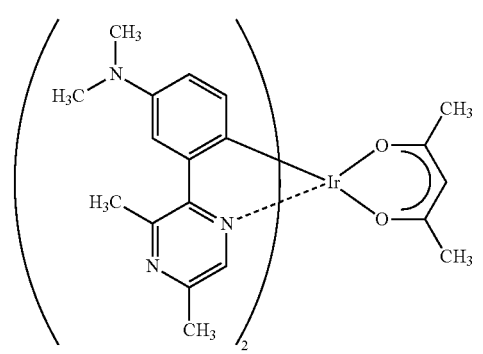
(110)
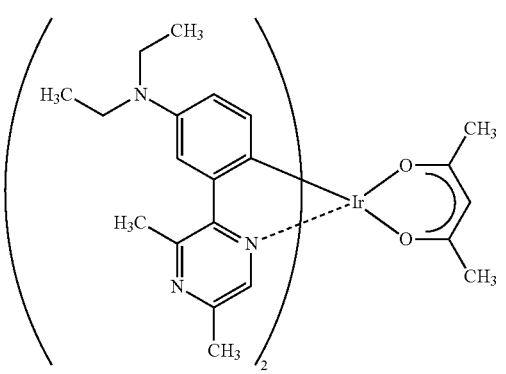
(114)
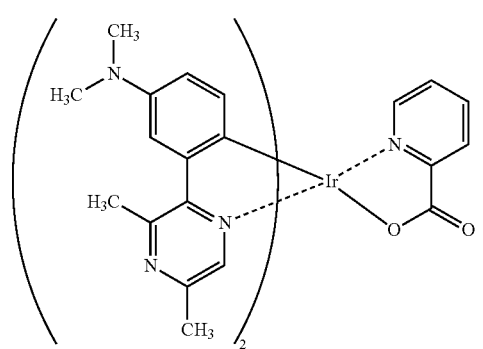
(111)
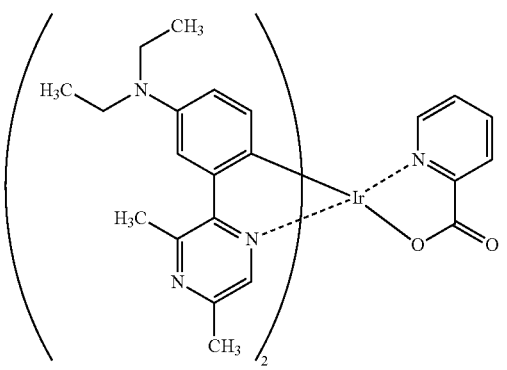
(115)

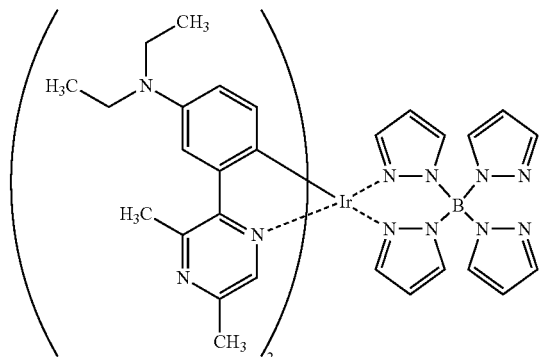
(116)
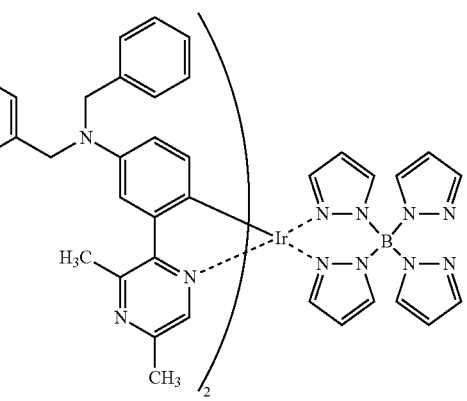
(120)
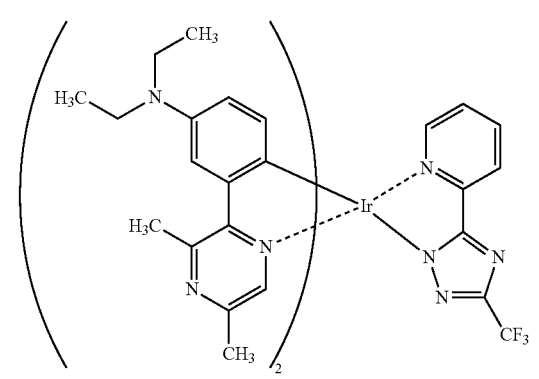
(117)
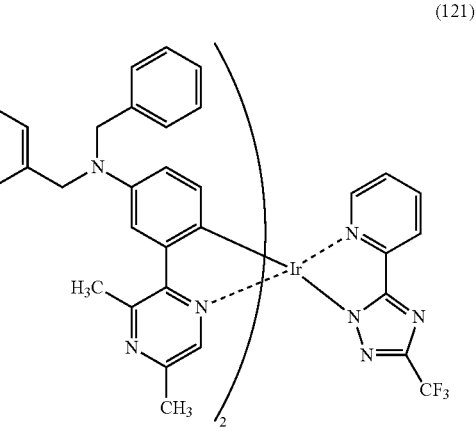
(121)
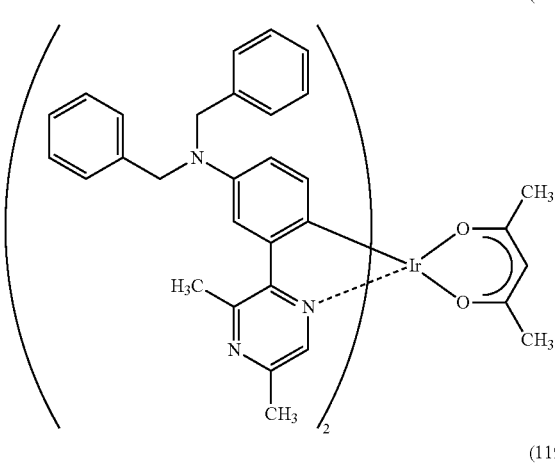
(118)
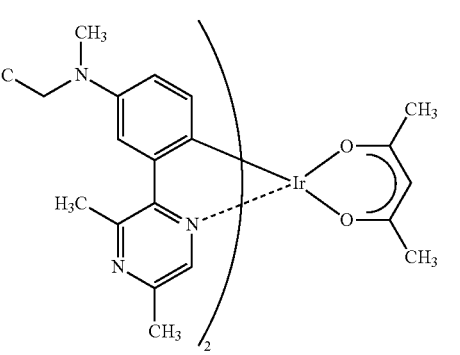
(122)
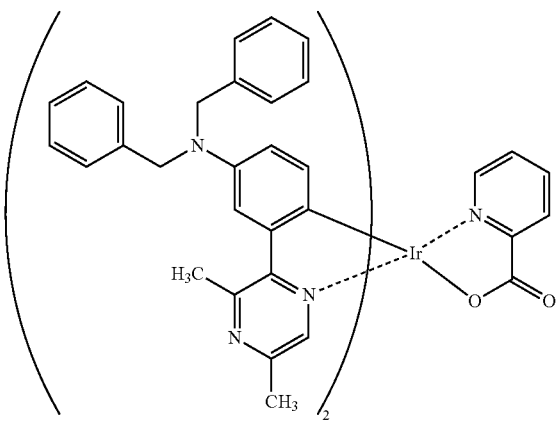
(119)
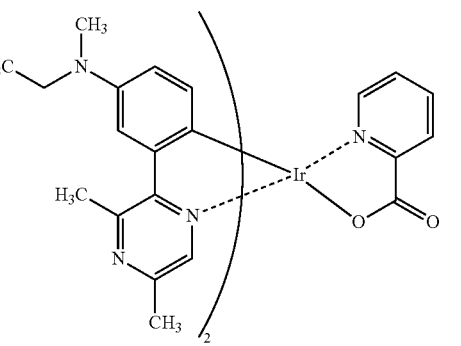
(123)

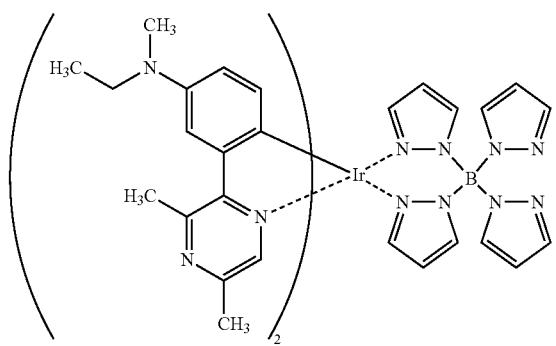
(124)
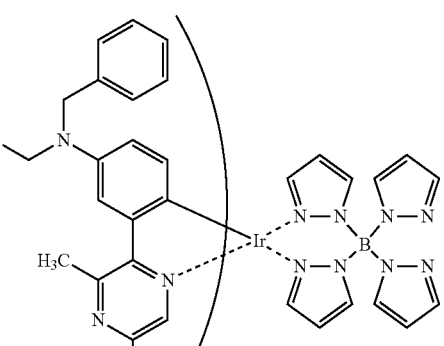
(128)
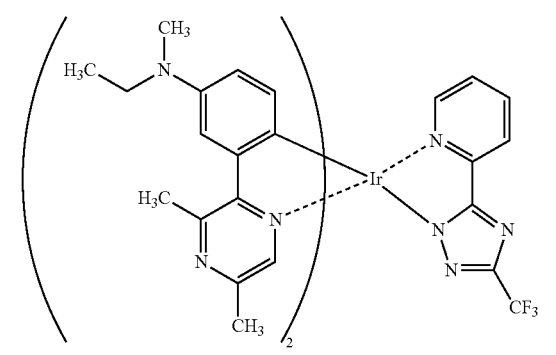
(125)
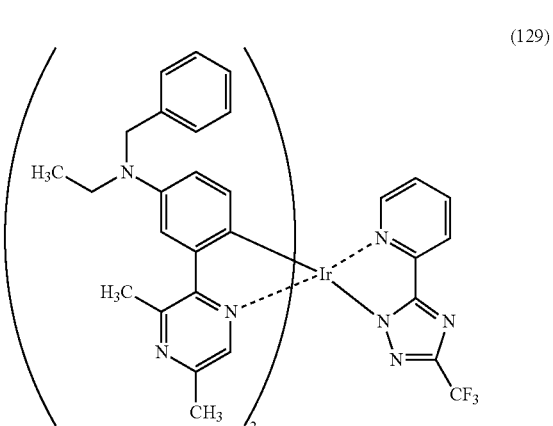
(129)
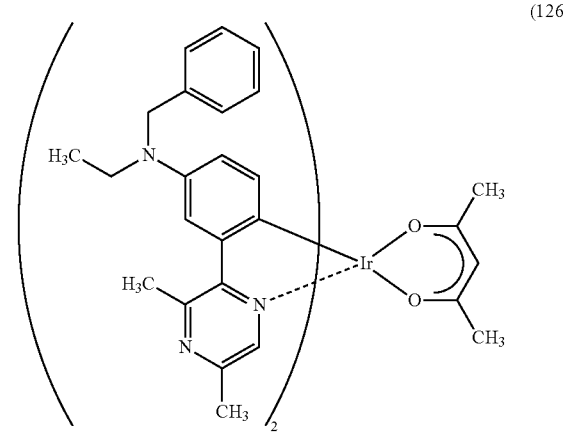
(126)
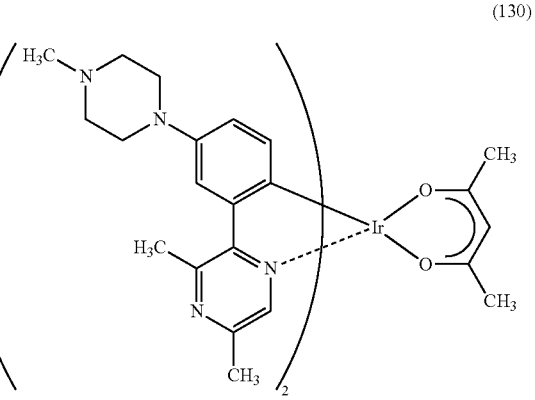
(130)
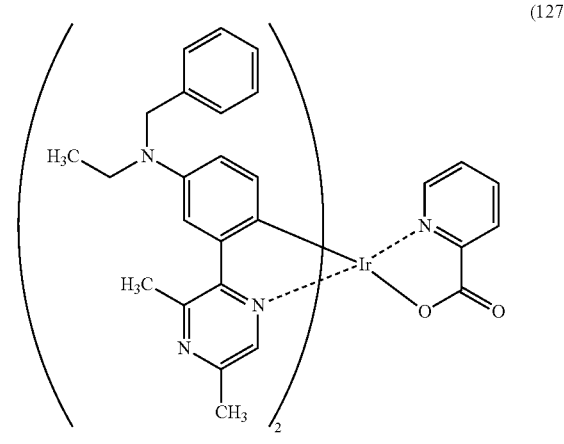
(127)
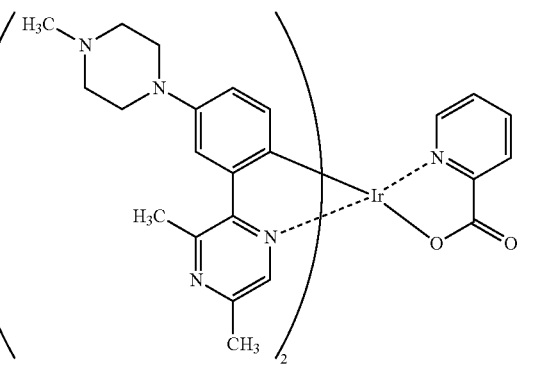
(131)

(132)
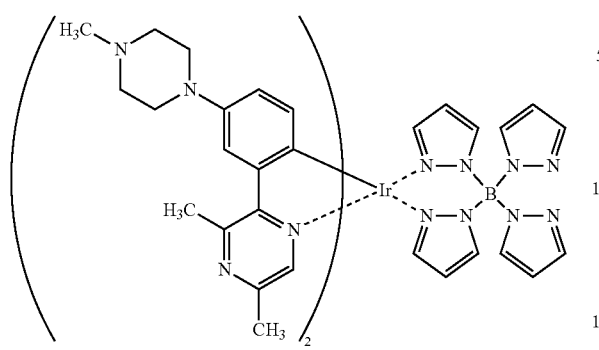
(133)
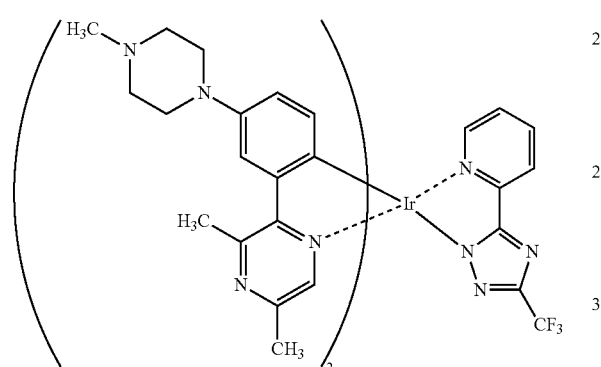
(134)
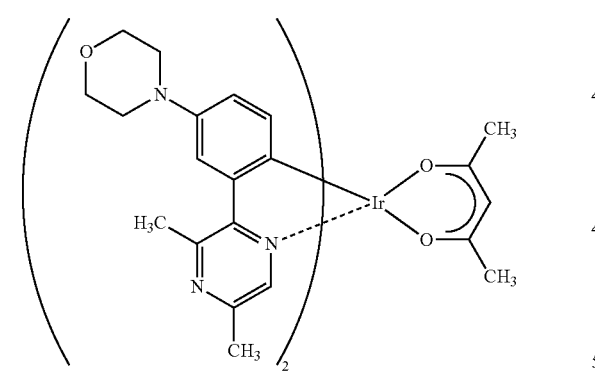
(135)
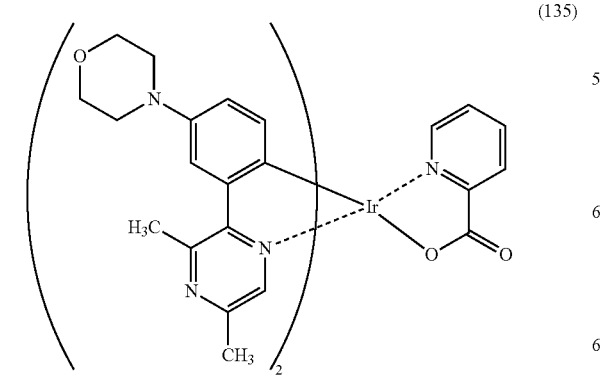
(136)
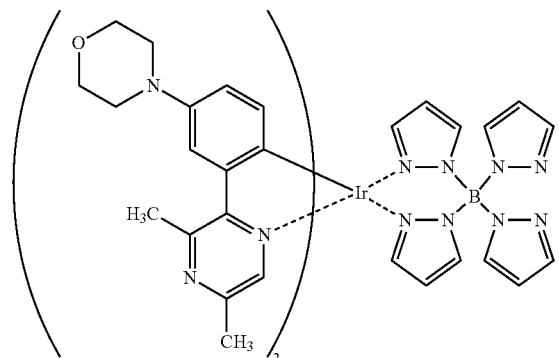
(137)
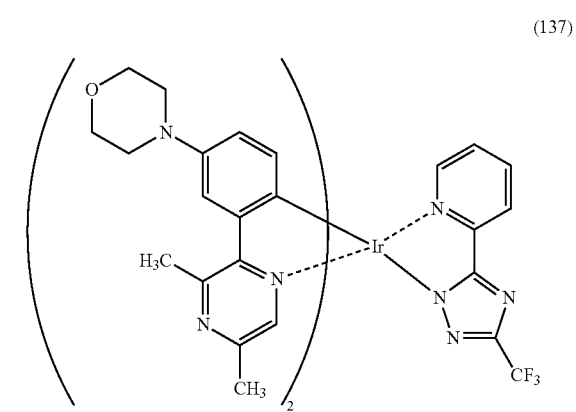
(138)
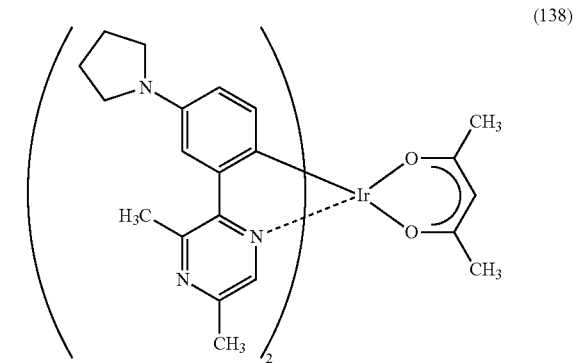
(139)
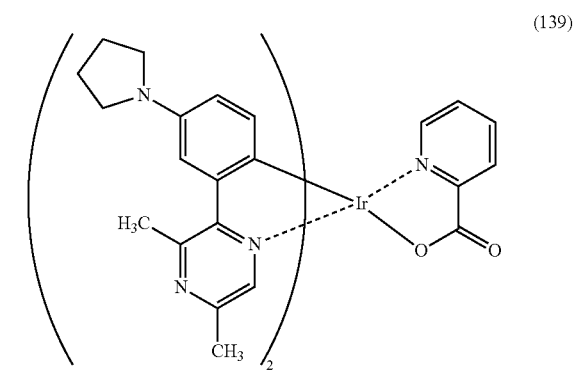

(140)
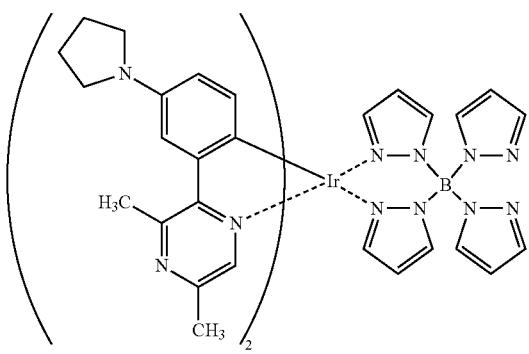
(141)
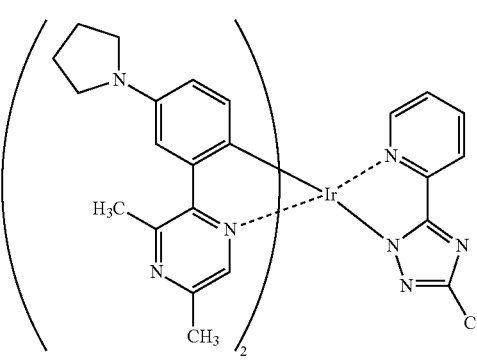
(142)
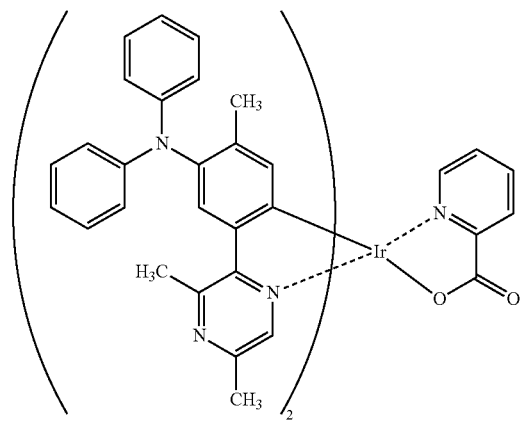
(143)
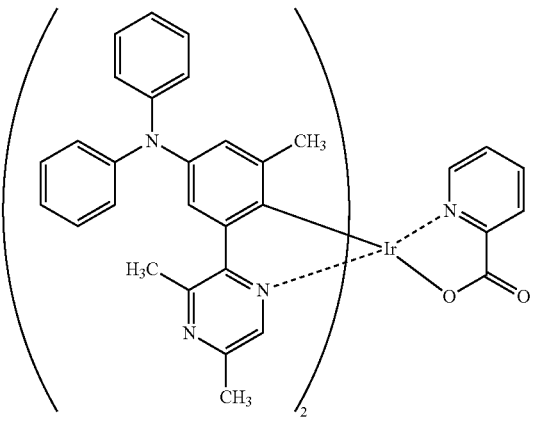
(144)
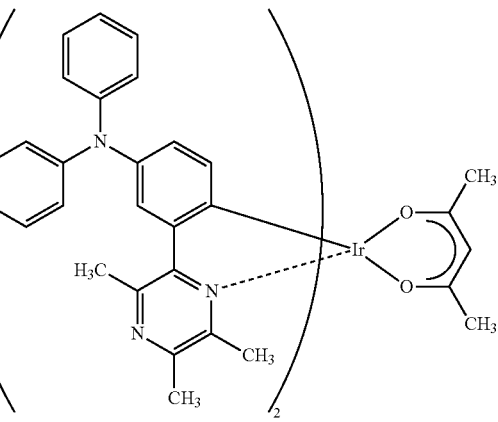
(145)
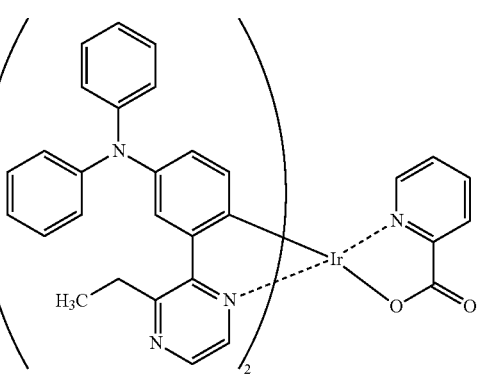
(146)
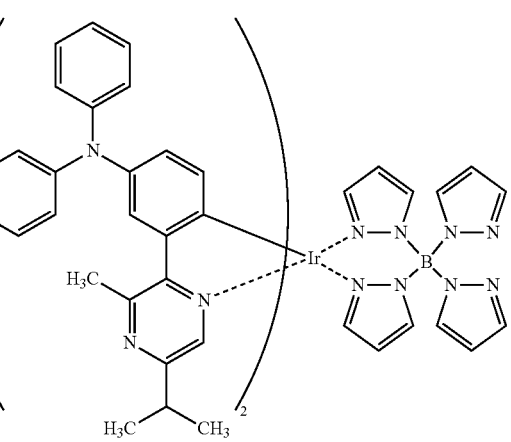

-continued

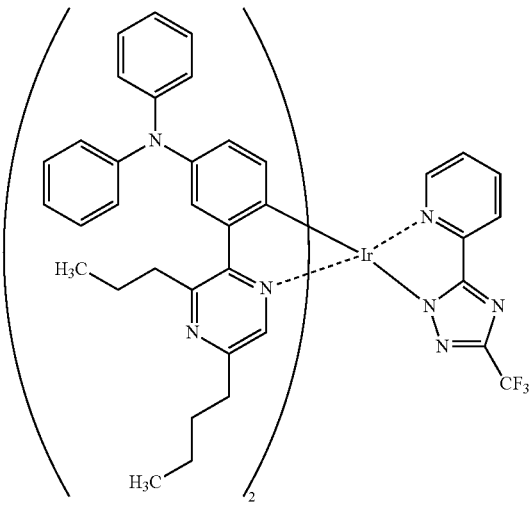

(147)

Note that there can be geometrical isomers and stereoisomers of the organometallic complexes represented by the structural formulas (100) to (147) depending on the type of ligand. The organometallic complex according to one embodiment of the present invention includes all of these isomers.

The above-described organometallic complexes according to embodiments of the present invention can be used as photosensitizers owing to the capability of intersystem crossing. Further, the organometallic complexes can be used as light-emitting materials or light-emitting substances in light-emitting elements owing to the capability of phosphorescence.

Embodiment 2

This embodiment shows a mode of a light-emitting element in which the organometallic complex according to one embodiment of the present invention is used for a light-emitting layer, with reference to FIG. 1.

FIG. 1 illustrates a light-emitting element having an EL layer 102 between a first electrode 101 and a second electrode 103. The light-emitting layer 113 contains any of the organometallic complexes which are embodiments of the present invention. This embodiment shows a case where the first electrode 101 serves as an anode and the second electrode 103 serves as a cathode.

When a voltage is applied between the first electrode 101 and the second electrode 103 of the light-emitting element illustrated in FIG. 1 so that a potential of the first electrode 101 is higher than that of the second electrode 103, holes are injected from the first electrode 101 side, and electrons are injected from the second electrode 103 side to the EL layer 102. Holes and electrons injected to the EL layer 102 recombine in the light-emitting layer 113 to produce an excited state of the organometallic complex according to one embodiment of the present invention. When the organometallic complex in the excited state relaxes to the ground state, light is emitted. Thus, the organometallic complex according to one embodiment of the present invention functions as a light-emitting substance in the light-emitting element.

In order to be used as an anode, the first electrode 101 is preferably formed using a metal, an alloy, an electrically conductive compound, a mixture thereof, or the like having a high work function (specifically, greater than or equal to 4.0 eV). Specific examples include a mixed oxide of indium oxide and tin oxide, a mixed oxide of indium oxide and zinc oxide, a mixed oxide of indium oxide and tin oxide containing silicon or silicon oxide, a mixed oxide of indium oxide and zinc oxide containing silicon or silicon oxide, gold (Au), platinum (Pt), nickel (Ni), tungsten (W), chromium (Cr), molybdenum (Mo), iron (Fe), cobalt (Co), copper (Cu), palladium (Pd), nitride of a metal material (for example, titanium nitride), and the like.

When a layer included in the EL layer 102 and formed in contact with the first electrode 101 is formed using a later-described composite material in which an organic compound and an electron acceptor (acceptor) are mixed, the first electrode 101 can be formed using any of a variety of metals, alloys, and electrically conductive compounds, a mixture thereof, and the like regardless of the work function. For example, aluminum (Al), silver (Ag), an alloy containing aluminum (e.g., AlSi), or the like can also be used.

The first electrode 101 can be formed by, for example, a sputtering method, an evaporation method (including a vacuum evaporation method), or the like.

The EL layer 102 formed over the first electrode 101 may include at least the light-emitting layer 113 containing the organometallic complex according to one embodiment of the present invention. For part of the EL layer 102, a known substance can be used, and either a low molecular compound or a high molecular compound can be used.

As illustrated in FIG. 1, the EL layer 102 is formed by stacking, in addition to the light-emitting layer 113, a hole-injection layer 111 containing a substance having a high hole-injection property, a hole-transport layer 112 containing a substance having a high hole-transport property, an electron-transport layer 114 containing a substance having a high electron-transport property, an electron-injection layer 115 containing a substance having a high electron-injection property, and the like, as appropriate.

The hole-injection layer 111 contains a substance having a high hole-injection property. As the substance having a high hole-injection property, a metal oxide can be used, such as molybdenum oxide, titanium oxide, vanadium oxide, rhenium oxide, ruthenium oxide, chromium oxide, zirconium oxide, hafnium oxide, tantalum oxide, silver oxide, tungsten oxide, or manganese oxide. Alternatively, a phthalocyanine compound can be used, such as phthalocyanine (abbreviation: H$_2$Pc), copper(II) phthalocyanine (abbreviation: CuPc), or vanadyl phthalocyanine (abbreviation: VOPc).

Alternatively, an aromatic amine compound which is a low molecular organic compound can be used, such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), or 3-[N-(1-naphthyl)-N-(9-phenylcarbazol-3-yl)amino]-9-phenylcarbazole (abbreviation: PCzPCN1).

Alternatively, a high molecular compound can be used, such as poly(N-vinylcarbazole) (abbreviation: PVK), poly (4-vinyltriphenylamine) (abbreviation: PVTPA), poly[N-(4-{N'-[4-(4-diphenylamino)phenyl]phenyl-N'- phenylamino}phenyl)methacrylamide] (abbreviation: PTPDMA), or poly[N,N'-bis(4-butylphenyl)-N,N'-bis(phenyl)benzidine] (abbreviation: Poly-TPD). Alternatively, a high molecular compound to which acid is added can be used, such as poly(3,4-ethylenedioxythiophene)/poly(styrenesulfonic acid) (PEDOT/PSS), or polyaniline/poly(styrenesulfonic acid) (PAni/PSS).

Alternatively, the hole-injection layer 111 may be formed using a composite material containing an organic compound and an electron acceptor (acceptor). Such a composite material is superior in a hole-injection property and a hole-transport property, since holes are generated in the organic compound by the electron acceptor. In this case, the organic compound is preferably a material excellent in transporting the generated holes (a substance having a high hole-transport property).

Examples of an organic compound that can be used for the composite material include various compounds; for example, it is possible to use a low molecular compound such as an aromatic amine compound, a carbazole derivative, an aromatic hydrocarbon compound, or a compound in which the basic skeleton is any of the low molecular compounds, such as oligomer, dendrimer, or polymer. The organic compound used for the composite material is preferably an organic compound having a high hole-transport property. Specifically, a substance having a hole mobility of $10^{-6}$ $cm^2/V \cdot s$ or higher is preferably used. However, another substance may also be used as long as the substance has a higher hole-transport property than an electron-transport property. The organic compounds which can be used for the composite material are specifically shown below.

Examples of the organic compound that can be used for the composite material include aromatic amine compounds such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB), and N,N'-bis(3-methylphenyl)-N,N'-diphenyl-[1,1'-biphenyl]-4,4'-diamine (abbreviation: TPD), and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)phenyl]-10-phenylanthracene (abbreviation: CzPA), and 1,4-bis[4-(N-carbazolyl)phenyl-2,3,5,6-tetraphenylbenzene.

Examples of the aromatic hydrocarbon compound include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, 2,3,6,7-tetramethyl-9,10-di(1-naphthyl)anthracene, and the like.

Examples of the aromatic hydrocarbon compound further include 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

As the electron acceptor, it is possible to use an organic compound such as 7,7,8,8-tetracyano-2,3,5,6-tetrafluoroquinodimethane (abbreviation: $F_4$-TCNQ) or chloranil, or a transition metal oxide. Alternatively, it is possible to use an oxide of a metal belonging to any of Groups 4 to 8 in the periodic table. Specifically, the following oxides are preferable because their electron-accepting property is high: vanadium oxide, niobium oxide, tantalum oxide, chromium oxide, molybdenum oxide, tungsten oxide, manganese oxide, and rhenium oxide. Among these, molybdenum oxide is especially preferable because it is stable in the air and its hygroscopic property is low and is easily treated.

Note that the hole-injection layer 111 may be formed using a composite material of any of the above-described high molecular compounds, such as PVK, PVTPA, PTPDMA, or Poly-TPD, and any of the above-described electron acceptors.

The hole-transport layer 112 contains a substance having a high hole-transport property. As the substance having a high hole-transport property, an aromatic amine compound can be used, such as NPB, TPD, 4,4'-bis[N-(9,9-dimethylfluoren-2-yl)-N-phenylamino]biphenyl (abbreviation: DFLDPBi), or 4,4'-bis[N-(spiro-9,9'-bifluoren-2-yl)-N-phenylamino]biphenyl (abbreviation: BSPB). The substances mentioned here are mainly ones that have a hole mobility of $10^{-6}$ $cm^2V \cdot s$ or higher. However, another substance may also be used as long as the substance has a higher hole-transport property than an electron-transport property. The layer containing a substance having a high hole-transport property is not limited to a single layer, and two or more layers containing the aforementioned substances may be stacked.

Alternatively, the hole-transport layer 112 can be formed using a high molecular compound such as PVK, PVTPA, PTPDMA, or Poly-TPD.

In the light-emitting layer 113, the organometallic complex according to one embodiment of the present invention is dispersed in an organic layer (a so-called host layer). The dispersed organometallic complex can prevent concentration quenching. The host layer is formed using a substance whose triplet excitation energy is higher than that of the organometallic complex. Therefore, the organometallic complex can emit light efficiently. Note that the triplet excitation energy indicates an energy difference between a ground state and a triplet excited state.

The material contained in the host layer used for dispersing the organometallic complex is preferably, but not limited to, any of compounds having an arylamine skeleton, such as 2,3-bis(4-diphenylaminophenyl)quinoxaline (abbreviation: TPAQn) and NPB, carbazole derivatives such as CBP and 4,4',4''-tris(N-carbazolyl)triphenylamine (abbreviation: TCTA), and metal complexes such as bis[2-(2-hydroxyphenyl)pyridinato]zinc (abbreviation: $Znpp_2$), bis[2-(2-hydroxyphenyl)benzoxazolato]zinc (abbreviation: $Zn(BOX)_2$), bis(2-methyl-8-quinolinolato)(4-phenylphenolato)aluminum (abbreviation: BAlq), and tris(8-quinolinolato)aluminum (abbreviation: $Alq_3$). Alternatively, a high molecular compound such as PVK can be used.

The electron-transport layer 114 contains a substance having a high electron-transport property. The electron-transport layer 114 can be formed using a metal complex such as $Alq_3$, tris(4-methyl-8-quinolinolato)aluminum (abbreviation: $Almq_3$), bis(10-hydroxybenzo[h]quinolinato)beryllium (abbreviation: $BeBq_2$), BAlq, $Zn(BOX)_2$, or bis[2-(2-hydroxyphenyl)benzothiazolato]zinc (abbreviation: $Zn(BTZ)_2$). In addition, it is possible to use a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation:

OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs). Further, it is possible to use a high molecular compound such as poly(2,5-pyridinediyl) (abbreviation: PPy), poly[(9,9-dihexylfluorene-2,7-diyl)-co-(pyridine-3,5-diyl)] (abbreviation: PPy) or poly[(9,9-dioctylfluorene-2,7-diyl)-co-(2,2'-bipyridine-6,6'-diyl)] (abbreviation: PF-BPy). The substances mentioned here are mainly ones that have an electron mobility of $10^{-6}$ cm$^2$V·s or higher. Note that any substance other than the above substances may be used for the electron-transport layer as long as the substance has a higher electron-transport property than a hole-transport property.

The electron-transport layer is not limited to a single layer, and two or more layers formed using the above substances may be stacked.

The electron-injection layer 115 contains a substance having a high electron-injection property. The electron-injection layer 115 can be formed using a fluoride or oxide of an alkali metal or an alkaline earth metal, such as lithium fluoride (LiF), cesium fluoride (CsF), calcium fluoride (CaF$_2$), or lithium oxide (LiO$_x$). Alternatively, a rare earth metal compound can be used, such as erbium fluoride (ErF$_3$). Further alternatively, it is possible to use the above substances for forming the electron-transport layer 114.

Alternatively, the electron-injection layer 115 may be formed using a composite material in which an organic compound and an electron donor (donor) are mixed. The composite material is superior in an electron-injection property and an electron-transport property, since electrons are generated in the organic compound by the electron donor. In this case, the organic compound is preferably a material excellent in transporting the generated electrons; specifically, it is possible to use the above substances for forming the electron-transport layer 114 (e.g., a metal complex or a heteroaromatic compound). As the electron donor, a substance exhibiting an electron-donating property to the organic compound may be used; specifically, it is preferable to use an alkali metal, an alkaline-earth metal, or a rare earth metal, such as lithium, cesium, magnesium, calcium, erbium, or ytterbium. Further, an alkali metal oxide or an alkaline-earth metal oxide is preferable, such as lithium oxide, calcium oxide, or barium oxide. Alternatively, Lewis base such as magnesium oxide can be used. Further alternatively, an organic compound such as tetrathiafulvalene (abbreviation: TTF) can be used.

Note that each of the above-described hole-injection layer 111, hole-transport layer 112, light-emitting layer 113, electron-transport layer 114, and electron-injection layer 115 can be formed by an evaporation method (including a vacuum evaporation method), an inkjet method, a coating method, or the like.

The second electrode 103 serves as a cathode. The cathode can be formed using a metal, an alloy, an electrically conductive compound, a mixture thereof, or the like which has a low work function (specifically, 3.8 eV or less). Specific examples include elements that belong to Group 1 or Group 2 of the periodic table, that is, alkali metals such as lithium (Li) and cesium (Cs) or alkaline earth metals such as magnesium (Mg), calcium (Ca), and strontium (Sr), or alloys thereof (e.g., MgAg and AlLi); rare earth metals such as europium (Eu) and ytterbium (Yb), or alloys thereof; aluminum (Al); silver (Ag); and the like.

The second electrode 103 can also be formed using aluminum, silver, a mixed oxide of indium oxide and tin oxide, a mixed oxide of indium oxide and zinc oxide, a mixed oxide of indium oxide and tin oxide containing silicon or silicon oxide, a mixed oxide of indium oxide and zinc oxide containing silicon or silicon oxide regardless of the work function. In this case, a layer included in the EL layer 102 and formed in contact with the second electrode 103 is formed using the above-described composite material in which an organic compound and an electron donor (donor) are mixed.

Note that the second electrode 103 can be formed by a vacuum evaporation method or a sputtering method. Alternatively, in the case of using a silver paste or the like, a coating method, an inkjet method, or the like can be used.

In the above-described light-emitting element, current flows due to a potential difference generated between the first electrode 101 and the second electrode 103, and holes and electrons recombine in the EL layer 102, whereby light is emitted. Then, this emitted light is extracted through either of the first electrode 101 or the second electrode 103, or both. For that purpose, either the first electrode 101 or the second electrode 103 or both has/have a light-transmitting property.

The use of the light-emitting element described in this embodiment makes it possible to manufacture a passive matrix light-emitting device or an active matrix light-emitting device in which the driving of the light-emitting element is controlled by a thin film transistor (TFT).

Note that there is no particular limitation on the structure of the TFT in the case of manufacturing an active matrix light-emitting device. For example, a staggered TFT or an inverted staggered TFT can be used as appropriate. Further, a driver circuit formed over a TFT substrate may be formed using both of an n-channel TFT and a p-channel TFT or only either an n-channel TFT or a p-channel TFT. Furthermore, there is no particular limitation on the crystallinity of a semiconductor film used for the TFT. For example, the semiconductor film can be an amorphous semiconductor film, a crystalline semiconductor film, an oxide semiconductor film, or the like.

The light-emitting element of this embodiment contains the organometallic complex according to one embodiment of the present invention, which emits red light with high color purity, in the light-emitting layer 113. As a result, the light-emitting element emits red light with high color purity.

The structure described in this embodiment can be combined with the structure described in Embodiment 1 as appropriate.

Embodiment 3

The light-emitting element which is one embodiment of the present invention may include a plurality of light-emitting layers. A plurality of light-emitting layers may be provided so that each of the light-emitting layers emits light, thereby obtaining a combination of light emission from the plurality of layers. Thus, white light emission can be obtained, for example. This embodiment shows a mode of a light-emitting element including a plurality of light-emitting layers, with reference to FIG. 2.

Figure 2:
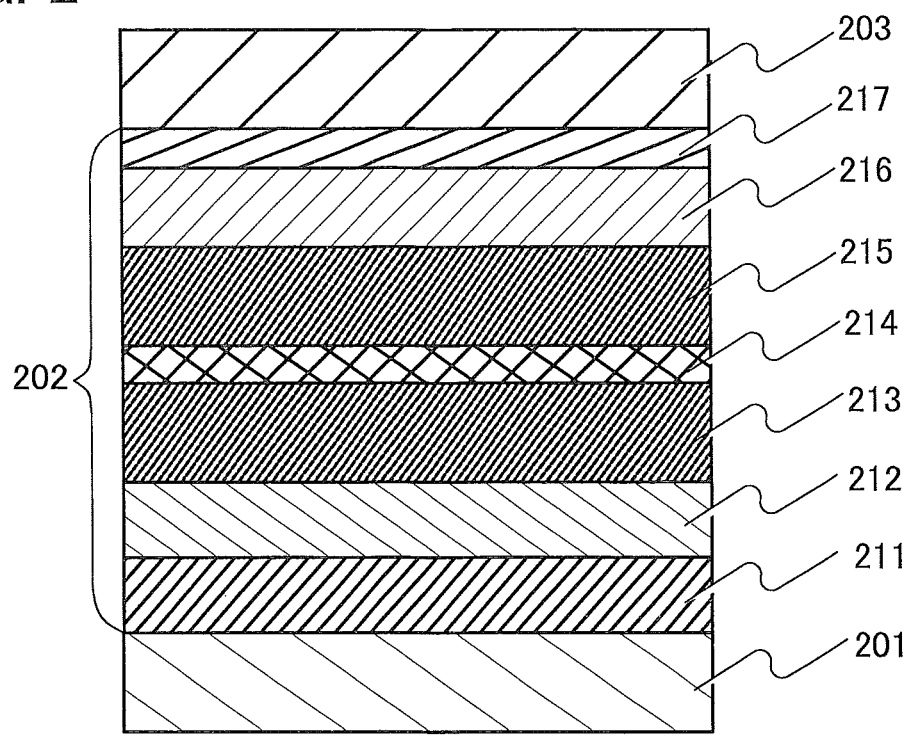
FIG. 2 is a view illustrating a light-emitting element according to one embodiment of the present invention.

As illustrated in FIG. 2, the light-emitting element is provided with a first light-emitting layer 213 and a second light-emitting layer 215 between a first electrode 201 and a second electrode 203. A separation layer 214 is preferably formed between the first light-emitting layer 213 and the second light-emitting layer 215.

Now, light emission of the element is described. By applying a voltage such that the potential of the first electrode 201 is higher than the potential of the second electrode 203, current flows between the first electrode 201 and the second electrode 203. As a result, holes and electrons recombine in any of the first light-emitting layer 213, the second light-emitting layer 215, and the separation layer 214. Generated excitation energy is distributed to both the first light-emitting layer 213 and the second light-emitting layer 215 to excite a first light-emitting substance contained in the first light-emitting layer 213 and a second light-emitting substance contained in the second light-emitting layer 215. The excited first and second light-emitting substances emit light while relaxing to the ground state. Thus, the light-emitting element can provide combination of light emission from the first light-emitting layer 213 and light emission from the second light-emitting layer 215.

The first light-emitting layer 213 contains the first light-emitting substance typified by a fluorescent compound such as perylene, 2,5,8,11-tetra(tert-butyl)perylene (abbreviation: TBP), DPVB 4,4'-bis[2-(N-ethylcarbazol-3-yl)vinyl]biphenyl (abbreviation: BCzVBi), BAlq, or bis(2-methyl-8-quinolinolato)galliumchloride (abbreviation: Gamq$_2$Cl); or a phosphorescent compound such as bis{2-[3,5-bis(trifluoromethyl)phenyl]pyridinato-N,C$^{2'}$}iridium(III)picolinate (abbreviation: Ir(CF$_3$ ppy)$_2$(pic)), bis[2-(4,6-difluorophenyl)pyridinato-N,C$^{2'}$]iridium(III)acetylacetonate (abbreviation: FIr(acac)), bis[2-(4,6-difluorophenyl)pyridinato-N, C$^{2'}$]iridium(III)picolinate (abbreviation: FIrpic), or bis[2-(4,6-difuluorophenyl)pyridinato-N,C$^{2'}$]iridium(III)tetra(1-pyrazolyl)borate (abbreviation: FIr6), which emits light having a peak at 450 nm to 510 nm in an emission spectrum (i.e., blue light to blue green light).

In addition, when the first light-emitting substance is a fluorescent compound, the first light-emitting layer 213 preferably has a structure in which a substance that has higher singlet excitation energy than the first light-emitting substance is used as a first host and the first light-emitting substance is dispersed as a guest. Further, when the first light-emitting substance is a phosphorescent compound, the first light-emitting layer 213 preferably has a structure in which a substance that has higher triplet excitation energy than the first light-emitting substance is used as a first host and the first light-emitting substance is dispersed as a guest. As the first host, DNA, t-BuDNA, or the like can be used in addition to the above-described NPB, CBP, TCTA, and the like. Note that the singlet excitation energy is an energy difference between a ground state and a singlet excited state. In addition, the triplet excitation energy is an energy difference between a ground state and a triplet excited state.

On the other hand, the second light-emitting layer 215 contains the organometallic complex which is one embodiment of the present invention and can emit red light. The second light-emitting layer 215 may have a structure similar to the light-emitting layer 113 described in Embodiment 2.

Specifically, the separation layer 214 can be formed using TPAQn, NPB, CBP, TCTA, Znpp$_2$, ZnBOX or the like described above. The thus provided separation layer 214 can prevent a defect that emission intensity of one of the first light-emitting layer 213 and the second light-emitting layer 215 is stronger than that of the other. Note that the separation layer 214 is not necessarily provided and may be provided as appropriate so that the ratio in emission intensity of the first light-emitting layer 213 and the second light-emitting layer 215 can be adjusted.

In this embodiment, the second light-emitting layer 215 is formed using the organometallic complex according to one embodiment of the present invention and the first light-emitting layer 213 is formed using any one of the first light-emitting substances listed above. Alternatively, the first light-emitting layer 213 may be formed using the organometallic complex according to one embodiment of the present invention and the second light-emitting layer 215 may be formed using any one of the first light-emitting substances.

Although this embodiment shows the light-emitting element in which two light-emitting layers are provided as illustrated in FIG. 2, the number of the light-emitting layers is not limited to two, and may be three for example. In addition, light emission from each light-emitting layer may be mixed. As a result, white light emission can be obtained, for example.

Note that the first electrode 201 may have a structure similar to that of the first electrode 101 described in Embodiment 2. In addition, the second electrode 203 may also have a structure similar to that of the second electrode 103 described in Embodiment 2.

Further, this embodiment shows a hole-injection layer 211, a hole-transport layer 212, an electron-transport layer 216, and an electron-injection layer 217 as illustrated in FIG. 2. As for structures of these layers, the structures of the respective layers described in Embodiment 2 may be applied. However, these layers are not necessarily provided and may be provided as appropriate according to element characteristics.

Note that the structure described in this embodiment can be combined with the structure described in Embodiment 1 or 2 as appropriate.

Embodiment 4

Figure 3:
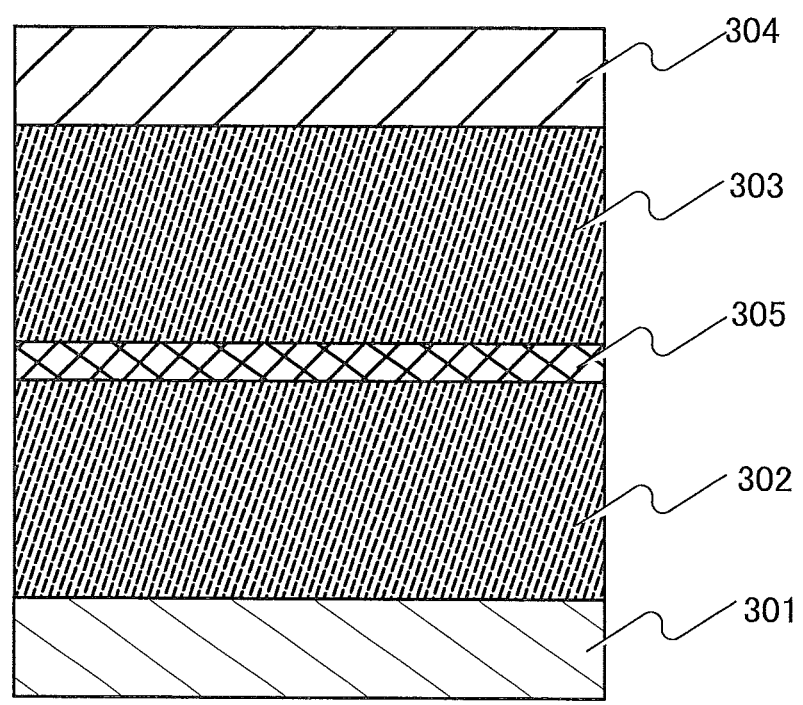
FIG. 3 is a view illustrating a light-emitting element according to one embodiment of the present invention.

This embodiment shows, as one embodiment of the present invention, a structure of a light-emitting element including a plurality of EL layers (hereinafter, such a light-emitting element is referred to as a stacked-type element) with reference to FIG. 3. This light-emitting element is a stacked-type light-emitting element including a plurality of EL layers (a first EL layer 302 and a second EL layer 303) between a first electrode 301 and a second electrode 304. Although this embodiment shows the case of two EL layers, three or more EL layers may be employed.

In this embodiment, the first electrode 301 functions as an anode, and the second electrode 304 functions as a cathode. Note that the first electrode 301 and the second electrode 304 can have structures similar to those described in Embodiment 2.

In addition, although the plurality of EL layers (the first EL layer 302 and the second EL layer 303) may have structures similar to those described in Embodiment 2, any of the EL layers may have a structure similar to that described in Embodiment 2. In other words, the structures of the first EL layer 302 and the second EL layer 303 may be the same or different from each other and can be similar to those described in Embodiment 2.

Further, a charge generation layer 305 is provided between the plurality of EL layers (the first EL layer 302 and the second EL layer 303). The charge generation layer 305 has a function of injecting electrons into one of the EL layers and injecting holes into the other of the EL layers when a voltage is applied between the first electrode 301 and the second electrode 304. In this embodiment, when a voltage is applied such that the potential of the first electrode 301 is higher than that of the second electrode 304, the charge generation layer 305 injects electrons into the first EL layer 302 and injects holes into the second EL layer 303.

Note that the charge generation layer 305 preferably has a light-transmitting property in terms of light extraction efficiency. Further, the charge generation layer 305 functions even if it has lower conductivity than the first electrode 301 or the second electrode 304.

The charge generation layer 305 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances mentioned here are mainly ones that have a hole mobility of $10^{-6}$ cm$^2$/V·s or higher. However, another substance may be used as long as the substance is an organic compound having a higher hole-transport property than an electron-transport property.

Further, as the electron acceptor, 7,7,8,8-tetracyano-2,3,5,6-tetrafluoroquinodimethane (abbreviation: F$_4$-TCNQ), chloranil, or the like can be used. Alternatively, a transition metal oxide can be used. Further alternatively, an oxide of metals that belong to Group 4 to Group 8 of the periodic table can be used. Specifically, it is preferable to use vanadium oxide, niobium oxide, tantalum oxide, chromium oxide, molybdenum oxide, tungsten oxide, manganese oxide, or rhenium oxide because the electron-accepting property is high. Among these, molybdenum oxide is especially preferable because it is stable in the air and its hygroscopic property is low and is easily treated.

On the other hand, in the case of the structure in which an electron donor is added to an organic compound having a high electron-transport property, the organic compound having a high electron-transport property can be used; for example, a metal complex having a quinoline skeleton or a benzoquinoline skeleton, such as Alq, Almq$_3$, BeBq$_2$, or BAlq, or the like can be used. Alternatively, it is possible to use a metal complex having an oxazole-based ligand or a thiazole-based ligand, such as Zn(BOX)$_2$ or Zn(BTZ)$_2$. Further alternatively, instead of a metal complex, it is possible to use PBD, OXD-7, TAZ, BPhen, BCP, or the like. The substances mentioned here are mainly ones that have an electron mobility of $10^{-6}$ cm$^2$/V·s or higher. Note that another substance may be used as long as the substance is an organic compound having a higher electron-transport property than a hole-transport property.

As the electron donor, it is possible to use an alkali metal, an alkaline earth metal, a rare earth metal, a metal belonging to Group 13 of the periodic table, or an oxide or carbonate thereof. Specifically, it is preferable to use lithium (Li), cesium (Cs), magnesium (Mg), calcium (Ca), ytterbium (Yb), indium (In), lithium oxide, cesium carbonate, or the like. Alternatively, an organic compound such as tetrathianaphthacene may be used as the electron donor.

Note that forming the charge generation layer 305 by using any of the above materials can suppress an increase in drive voltage caused by the stack of the EL layers.

Although this embodiment shows the light-emitting element having two EL layers, the present invention can be similarly applied to a light-emitting element in which three or more EL layers are stacked. As in the light-emitting element according to this embodiment, when a charge generation layer is interposed between a plurality of EL layers between a pair of electrodes, light emission in a high luminance region can be obtained. Since the current density can be kept low, the element can have a long lifetime. When the light-emitting element is applied for illumination, voltage drop due to resistance of an electrode material can be reduced, thereby achieving homogeneous light emission in a large area. Moreover, it is possible to achieve a light-emitting device of low power consumption, which can be driven at a low voltage.

By making the EL layers emit light of different colors from each other, the light-emitting element can provide light emission of a desired color as a whole. For example, by forming a light-emitting element having two EL layers such that the emission color of the first EL layer and the emission color of the second EL layer are complementary colors, the light-emitting element can provide white light emission as a whole. Note that the word "complementary" means color relationship in which an achromatic color is obtained when colors are mixed. That is, when complementary colored light emitted from substances is mixed, white-light emission can be obtained.

Further, the same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined with any of the structures described in Embodiments 1 to 3 as appropriate.

Embodiment 5

This embodiment shows, as one embodiment of the present invention, a mode of a light-emitting element in which an organometallic complex is used as a sensitizer, with reference to FIG. 1.

FIG. 1 illustrates a light-emitting element in which the EL layer 102 including the light-emitting layer 113 is interposed between the first electrode 101 and the second electrode 103. The light-emitting layer 113 contains the organometallic complex which is one embodiment of the present invention and a fluorescent compound which can emit light having a longer wavelength than the organometallic complex.

In such a light-emitting element, holes injected from the first electrode 101 side and electrons injected from the second electrode 103 side recombine in the light-emitting layer 113 to bring the fluorescent compound into an excited state. The excited fluorescent compound emits light while relaxing to the ground state. In this case, the organometallic complex which is one embodiment of the present invention acts as a sensitizer for the fluorescent compound to increase the number of molecules of fluorescent compounds in singlet excited states. In the above manner, the organometallic complex which is one embodiment of the present invention can be used as a sensitizer so as to achieve a light-emitting element with high emission efficiency. Note that in the light-emitting element of this embodiment, the first electrode 101 functions as an anode and the second electrode 103 function as a cathode.

The light-emitting layer 113 contains the organometallic complex which is one embodiment of the present invention and the fluorescent compound which can emit light having a longer wavelength than the organometallic complex. In the light-emitting layer 113, it is preferable that a substance having higher triplet excitation energy than the organometallic complex and higher singlet excitation energy than the fluorescent compound be used as a host and the organometallic complex and the fluorescent compound be dispersed as a guest.

Note that there is no particular limitation on the substance used for dispersing the organometallic complex and the fluorescent compound (i.e., host), and the substances given as examples of the host in Embodiment 2, or the like can be used.

Although there is no particular limitation on the fluorescent compound, it is preferable to use a compound which emits red light to infrared light, such as 4-dicyanomethylene-2-isopropyl-6-[2-(1,1,7,7-tetramethyljulolidin-9-yl) ethenyl]-4H-py ran (abbreviation: DCJTI), magnesium phthalocyanine, magnesium porphyrin, phthalocyanine, or the like.

Note that the first electrode 101 and the second electrode 103 described in this embodiment may have structures similar to those of the first electrode and the second electrode described in Embodiment 2, respectively.

As illustrated in FIG. 1, the hole-injection layer 111, the hole-transport layer 112, the electron-transport layer 114, and the electron-injection layer 115 are provided in this embodiment; structures thereof may be those of the respective layers described in Embodiment 2. However, these layers are not necessarily provided and may be provided as appropriate according to element characteristics.

The above-described light-emitting element can emit light with high efficiency by use of the organometallic complex which is one embodiment of the present invention as a sensitizer.

Note that the structure described in this embodiment can be combined with any of the structures described in Embodiments 1 to 4 as appropriate.

Embodiment 6

This embodiment shows, as one embodiment of the present invention, a passive matrix light-emitting device and an active matrix light-emitting device each of which is a light-emitting device fabricated using a light-emitting element.

FIGS. 4A to 4D and FIG. 5 illustrate examples of passive matrix light-emitting devices.

The passive matrix (also called simple matrix) light-emitting device exemplified in this embodiment includes a plurality of anodes arranged in stripes (in stripe form) and a plurality of cathodes arranged in stripes. The plurality of anodes are provided to intersect with the plurality of cathodes, and intersecting portions arranged in matrix form pixel portions. In each of the intersecting portions of the anodes and the cathodes, a light-emitting layer is interposed therebetween. Accordingly, voltage application between one anode and one cathode causes a light-emitting layer at the intersecting portion (i.e., a pixel) to emit light.

Figure 4A:
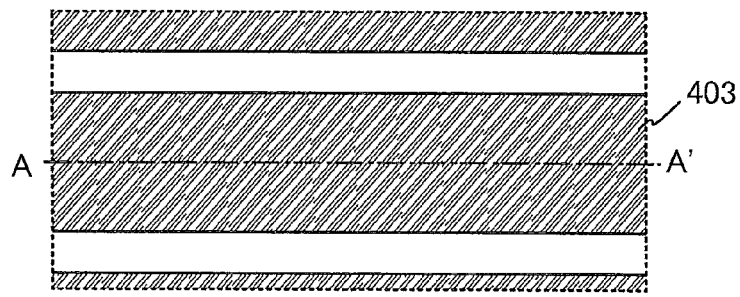
FIGS. 4A to 4D are views illustrating a passive matrix light-emitting device.
Figure 4B:
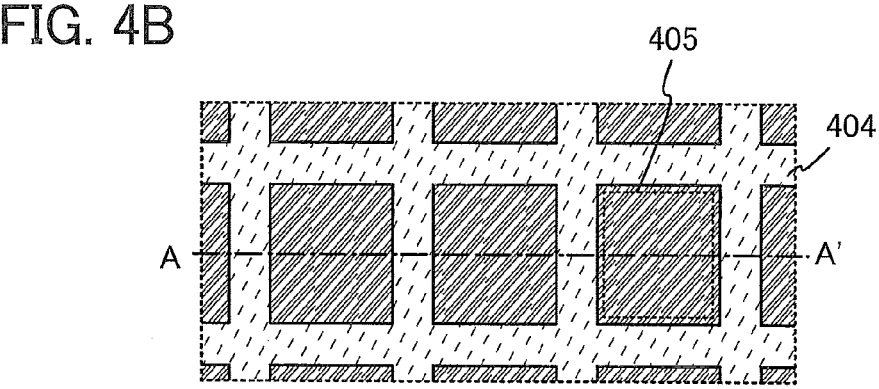
Figure 4C:
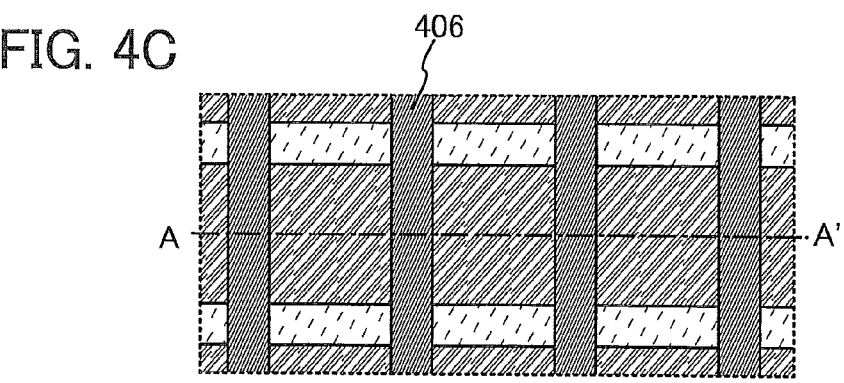
Figure 4D:
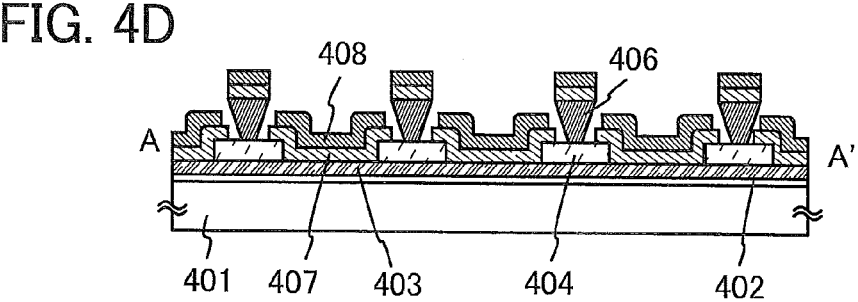

FIGS. 4A to 4C are top views of a pixel portion. FIG. 4D is a cross-sectional view taken along the chain line A-N in FIGS. 4A to 4C. Note that there is no illustration of a structure in which the light-emitting element is sealed.

An insulating layer 402 is provided as a base insulating layer over a substrate 401; however, the base insulating layer is not necessarily provided. A plurality of first electrodes 403 are provided over the insulating layer 402 (see FIG. 4D).

Note that the plurality of first electrodes 403 are arranged in stripes at regular intervals over the insulating layer 402 (see FIG. 4A).

In addition, a partition 404 having openings 405 each corresponding to a pixel is provided over the first electrodes 403. The partition 404 having the openings 405 is formed using an insulating material (a photosensitive or nonphotosensitive organic material (e.g., polyimide, acrylic, polyamide, polyimide amide, resist, or benzocyclobutene) or an SOG film (e.g., a $SiO_x$ film containing an alkyl group)). Note that the openings 405 each corresponding to a pixel serve as light-emitting regions (FIG. 4B).

Over the partition 404 having the openings 405, a plurality of inversely tapered partitions 406 which are parallel to each other is provided to intersect with the first electrodes 403 (FIG. 4C). The inversely tapered partitions 406 are formed by a photolithography method using a positive photosensitive resin, portion of which unexposed to light remains as a pattern, and by adjustment of the amount of light exposure or the length of development time so that a lower portion of a pattern is etched more.

After the inversely tapered partitions 406 are formed as illustrated in FIG. 4C, EL layers 407 and second electrodes 408 are sequentially formed as illustrated in FIG. 4D. The total thickness of the partition 404 having the openings 405 and the inversely tapered partition 406 is set to be larger than the total thickness of the EL layer 407 and the second electrode 408; thus, as illustrated in FIG. 4D, EL layers 407 and second electrodes 408 which are divided into plural regions are formed. Note that the plurality of divided regions are electrically isolated from one another.

The second electrodes 408 are electrodes in stripe form that are parallel to each other and extend along a direction intersecting with the first electrodes 403. Note that parts of a layer for forming the EL layers 407 and parts of a conductive layer for forming the second electrodes 408 are also formed over the inversely tapered partitions 406; however, these parts are separated from the EL layers 407 and the second electrodes 408.

Note that in this embodiment, the first electrode 403 may function as an anode and the second electrode 408 may function as a cathode, or vice versa. Note that a stacked structure including the EL layer 407 may be adjusted as appropriate in accordance with the polarity of the electrode.

Further, if necessary, a sealing material such as a sealing can or a glass substrate may be attached to the substrate 401 for sealing with an adhesive such as a sealant, so that the light-emitting element is placed in the sealed space. Thereby, deterioration of the light-emitting element can be prevented. The sealed space may be filled with filler or a dry inert gas. Further, a desiccant or the like may be put between the substrate and the sealing material in order to prevent deterioration of the light-emitting element due to moisture or the like. The desiccant removes a minute amount of moisture, thereby achieving sufficient desiccation. The desiccant may be a substance which absorbs moisture by chemical adsorption such as an oxide of an alkaline earth metal as typified by calcium oxide or barium oxide. Additionally, a substance which adsorbs moisture by physical adsorption such as zeolite or silica gel may be used as well, as a desiccant.

Figure 5:
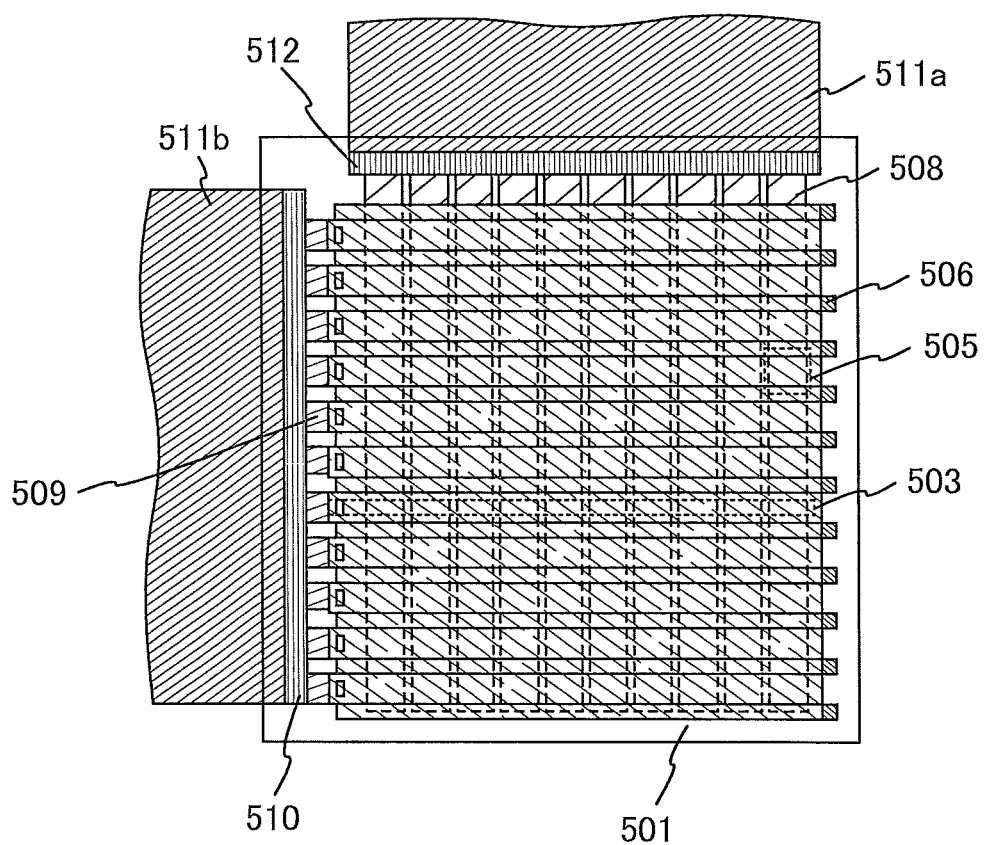
FIG. 5 is a view illustrating a passive matrix light-emitting device.

FIG. 5 is a top view of the case where the passive matrix light-emitting device illustrated in FIGS. 4A to 4D is mounted with an FPC and the like.

As illustrated in FIG. 5, in a pixel portion forming an image display, scanning lines and data lines intersect with each other so that they are orthogonal to each other.

Here, the substrate 401, the first electrode 403, the second electrode 408, and the inversely tapered partition 406 in FIGS. 4A to 4D correspond to a substrate 501, a scan line 503, a data line 508, and a partition 506 in FIG. 5, respectively. The EL layers 407 in FIGS. 4A to 4D are interposed between the data lines 508 and the scan lines 503, and an intersection portion indicated by a region 505 corresponds to one pixel.

Note that the scan lines 503 are electrically connected at their ends to connection wirings 509, and the connection wirings 509 are connected to an FPC 511b through an input terminal 510. In addition, the data lines 508 are connected to an FPC 511a through the input terminal 512.

If necessary, a polarizing plate, a circularly polarizing plate (including an elliptically polarizing plate), a retardation plate (a quarter-wave plate or a half-wave plate), or an optical film such as a color filter may be provided as appropriate over a light-emitting surface. Further, the polarizing plate or the circularly polarizing plate may be provided with an anti-reflection film. For example, anti-glare treatment can be performed so that reflected light can be diffused by projections and depressions on the surface to reduce the glare.

Although FIG. 5 illustrates an example in which a driver circuit is not provided over the substrate, an IC chip including a driver circuit may be mounted over the substrate.

When the IC chip is mounted, a data line side IC and a scan line side IC, in each of which a driver circuit for transmitting a signal to a pixel portion is formed, are mounted on the periphery of the pixel portion (outside the pixel portion) by a COG method. The mounting may be performed using a TCP or a wire bonding method other than the COG method. The TCP is a TAB tape mounted with the IC, and the TAB tape is connected to a wiring over an element formation substrate to mount the IC. Each of the data line side IC and the scan line side IC may be formed using a silicon substrate, or may be formed using a glass substrate, a quartz substrate, or a plastic substrate over which a driver circuit is formed using TFTs.

Figure 6A:
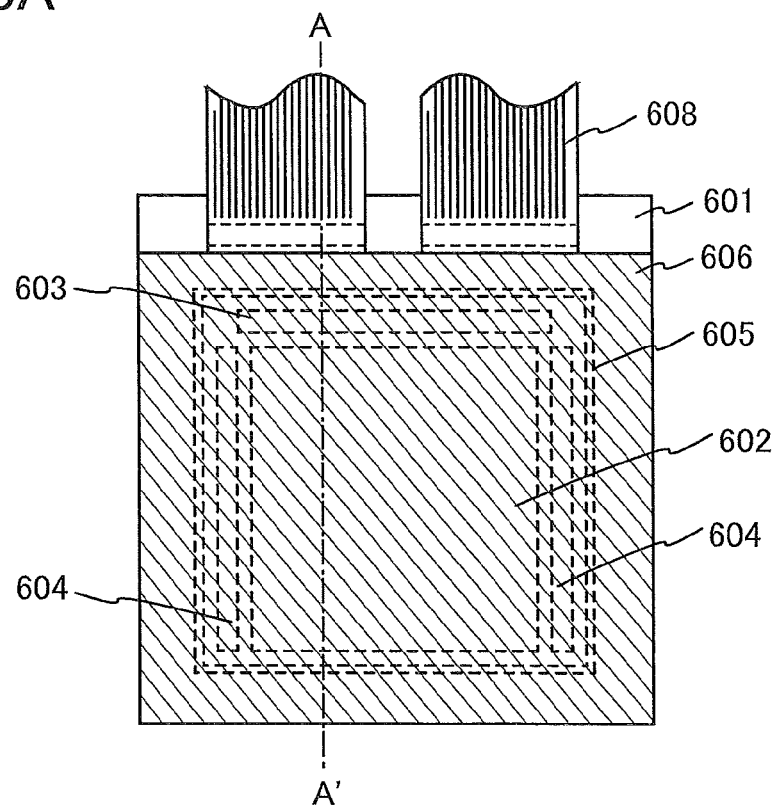
FIGS. 6A and 6B are views illustrating an active matrix light-emitting device.
Figure 6B:
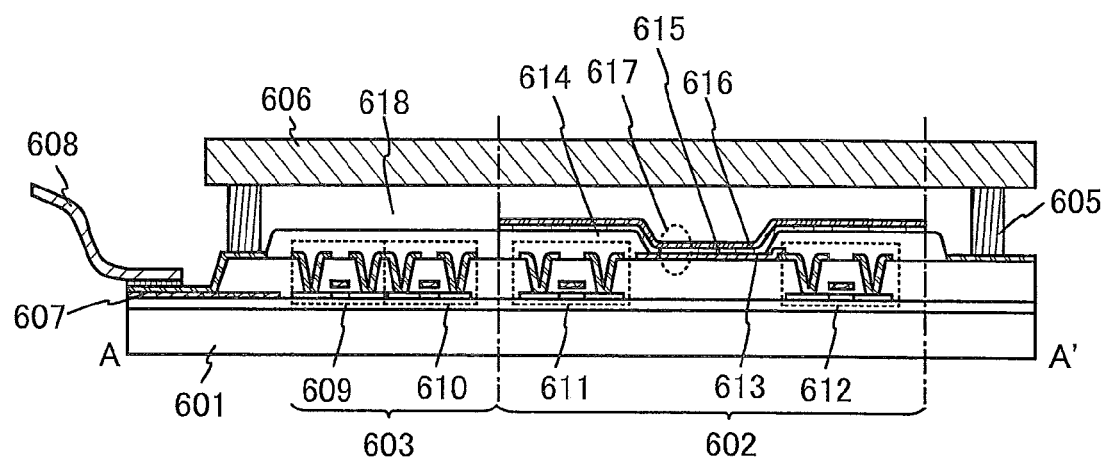

Next, an example of an active matrix light-emitting device is described with reference to FIGS. 6A and 6B. Note that FIG. 6A is a top view illustrating a light-emitting device and FIG. 6B is a cross-sectional view taken along the chain line A-A' in FIG. 6A. The active matrix light-emitting device according to this embodiment includes a pixel portion 602 provided over an element substrate 601, a driver circuit portion (a source side driver circuit) 603, and a driver circuit portion (a gate side driver circuit) 604. The pixel portion 602, the driver circuit portion (source side driver circuit) 603, and the driver circuit portion (gate side driver circuit) 604 are sealed between the element substrate 601 and the sealing substrate 606 by a sealant 605.

In addition, there is provided a lead wiring 607 over the element substrate 601. The lead wiring 607 is provided for connecting an external input terminal through which a signal (e.g., a video signal, a clock signal, a start signal, and a reset signal) or a potential from the outside is transmitted to the driver circuit portion (source side driver circuit) 603 and the driver circuit portion (gate side driver circuit) 604. Here is shown an example in which a flexible printed circuit (FPC) is provided as the external input terminal. Although an FPC 608 is illustrated alone, this FPC may be provided with a printed wiring board (PWB). The light-emitting device in this specification includes, in its category, not only the light-emitting device itself but also the light-emitting device to which the FPC or the FPC provided with the PWB is attached.

Next, a cross-sectional structure is described with reference to FIG. 6B. The driver circuit portion and the pixel portion are formed over the element substrate 601; here are illustrated the driver circuit portion (source side driver circuit) 603 which is the source driver circuit and the pixel portion 602.

The driver circuit portion (source side driver circuit) 603 is an example where a CMOS circuit is formed, which is a combination of an n-channel TFT 609 and a p-channel TFT 610. Note that a circuit included in the driver circuit portion may be formed using various CMOS circuits, PMOS circuits, or NMOS circuits. Although this embodiment shows a driver integrated type in which the driver circuit is formed over the substrate, the driver circuit is not necessarily formed over the substrate, and the driver circuit can be formed outside, not over the substrate.

The pixel portion 602 is formed of a plurality of pixels each of which includes a switching TFT 611, a current control TFT 612, and an anode 613 which is electrically connected to a wiring (a source electrode or a drain electrode) of the current control TFT 612. Note that an insulator 614 is formed to cover end portions of the anode 613. In this embodiment, the insulator 614 is formed using a positive photosensitive acrylic resin.

The insulator 614 preferably has a curved surface with curvature at an upper end portion or a lower end portion thereof in order to obtain favorable coverage by a film which is to be stacked over the insulator 614. For example, in the case of using a positive photosensitive acrylic resin as a material for the insulator 614, the insulator 614 preferably has a curved surface with a curvature radius (0.2 μm to 3 μm) at the upper end portion. Note that the insulator 614 can be formed using either a negative photosensitive material that becomes insoluble in an etchant by light irradiation or a positive photosensitive material that becomes soluble in an etchant by light irradiation. It is possible to use, without limitation to an organic compound, either an organic compound or an inorganic compound such as silicon oxide or silicon oxynitride.

An EL layer 615 and a cathode 616 are stacked over the anode 613. Note that it is preferable that the anode 613 be formed using an indium tin oxide film, and that a wiring of the current-controlling TFT 612 connected to the anode 613 be formed using a stacked film of a titanium nitride film and a film containing aluminum as its main component or a stacked film of a titanium nitride film, a film containing aluminum as its main component, and a titanium nitride film. This structure achieves low resistance of the wiring and favorable ohmic contact with the indium tin oxide film. Although not illustrated in FIGS. 6A and 6B, the cathode 616 is electrically connected to an FPC 608 which is an external input terminal.

The EL layer 615 includes at least a light-emitting layer. The EL layer 615 is provided with, in addition to the light-emitting layer, a hole-injection layer, a hole-transport layer, an electron-transport layer, or an electron-injection layer, as appropriate. A light-emitting element 617 is formed of a stacked structure of the anode 613, the EL layer 615, and the cathode 616.

Although the cross-sectional view of FIG. 6B illustrates only one light-emitting element 617, a plurality of light-emitting elements are arranged in matrix in the pixel portion 602. Light-emitting elements which provide three kinds of light emission (R, G and B) are selectively formed in the pixel portion 602, whereby a light-emitting device capable of full color display can be fabricated. Alternatively, a light-emitting device which is capable of full color display may be fabricated by a combination with color filters.

Further, the sealing substrate 606 is attached to the element substrate 601 with the sealant 605, whereby a light-emitting element 617 is provided in a space 618 surrounded by the element substrate 601, the sealing substrate 606, and the sealant 605. The space 618 may be filled with an inert gas (such as nitrogen or argon), or the sealant 605.

An epoxy based resin is preferably used for the sealant 605. It is desirable that materials used for the sealant 605 do not transmit moisture or oxygen as much as possible. As the sealing substrate 606, a plastic substrate formed of FRP (fiberglass-reinforced plastics), PVF (polyvinyl fluoride), polyester, or acrylic can be used instead of a glass substrate or a quartz substrate.

As described above, an active matrix light-emitting device can be obtained.

Note that the structure described in this embodiment can be combined with any of the structures described in Embodiments 1 to 5 as appropriate.

Embodiment 7

This embodiment shows, with reference to FIGS. 7A to 7E and FIG. 8, examples of a variety of electronic devices and lighting devices that are completed by using any light-emitting device which is one embodiment of the present invention.

Examples of the electronic devices to which the light-emitting device is applied include television sets (also referred to as televisions or television receivers), monitors of computers or the like, cameras such as digital cameras or digital video cameras, digital photo frames, cellular phones (also referred to as mobile phones or cellular phone sets), portable game consoles, portable information terminals, audio reproducing devices, large game machines such as pachinko machines, and the like. Specific examples of these electronic devices and lighting device are illustrated in FIGS. 7A to 7E.

Figure 7A:
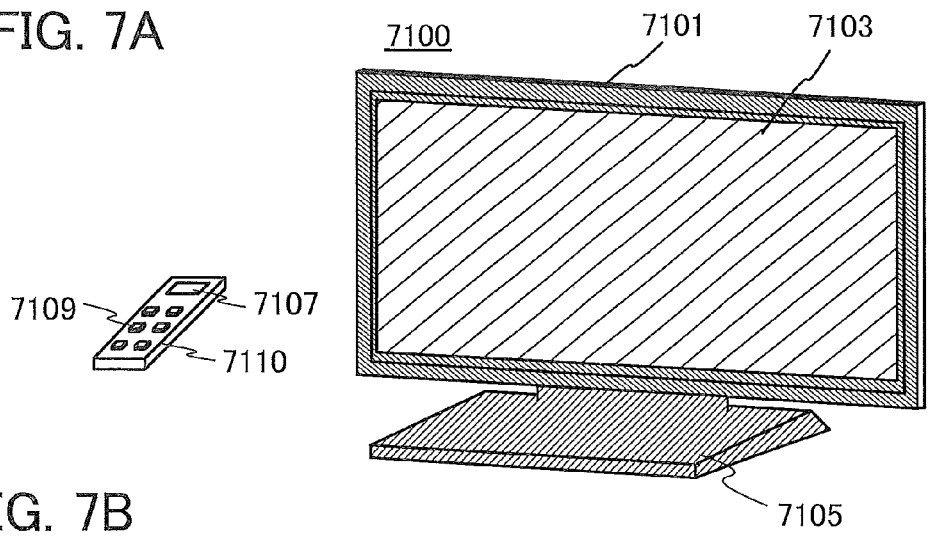
FIGS. 7A to 7E are views illustrating electronic devices.

FIG. 7A illustrates an example of a television device. In a television device 7100, a display portion 7103 is incorporated in a housing 7101. Images can be displayed by the display portion 7103, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Further, the remote controller 7110 may be provided with a display portion 7107 for displaying data output from the remote controller 7110.

Note that the television device 7100 is provided with a receiver, a modem, and the like. With the use of the receiver, general television broadcasting can be received. Moreover, when the display device is connected to a communication network with or without wires via the modem, one-way (from a sender to a receiver) or two-way (between a sender and a receiver or between receivers) information communication can be performed.

Figure 7B:
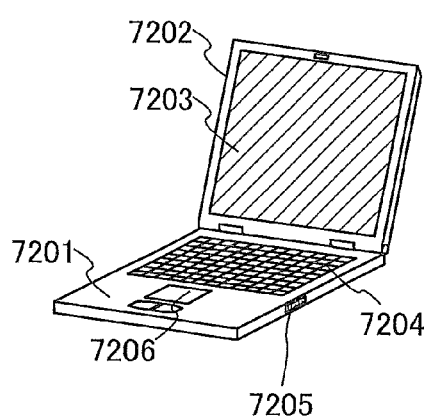

FIG. 7B illustrates a computer, which includes a main body 7201, a housing 7202, a display portion 7203, a keyboard 7204, an external connection port 7205, a pointing device 7206, and the like. This computer is manufactured by using a light-emitting device for the display portion 7203.

Figure 7C:
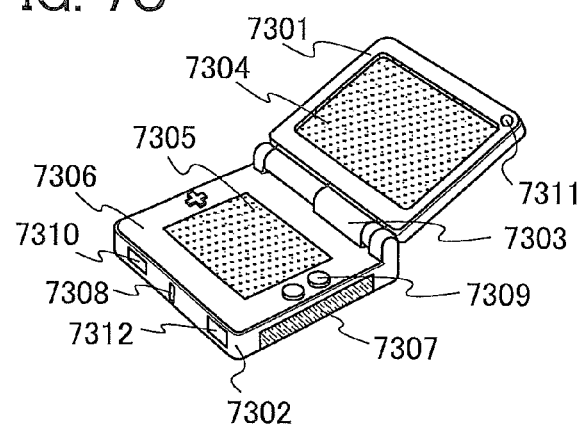

FIG. 7C illustrates a portable game machine, which includes two housings, a housing 7301 and a housing 7302, which are connected with a joint portion 7303 so that the portable game machine can be opened or folded. A display portion 7304 is incorporated in the housing 7301 and a display portion 7305 is incorporated in the housing 7302. In addition, the portable game machine illustrated in FIG. 7C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable game machine is not limited to the above as long as the light-emitting device is used for at least either the display portion 7304 or the display portion 7305, or both, and can include other accessories arbitrarily. The portable game machine illustrated in FIG. 7C has a function of reading out a program or data stored in a storage medium to display it on the display portion, and a function of sharing information with another portable game machine by wireless communication. The portable game machine illustrated in FIG. 7C can have a variety of functions without limitation to the above.

Figure 7D:
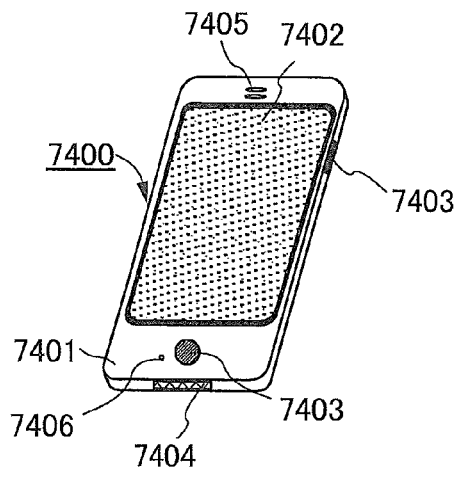

FIG. 7D illustrates an example of a cellular phone. The cellular phone 7400 is provided with a display portion 7402 incorporated in a housing 7401, operation buttons 7403, an external connection port 7404, a speaker 7405, a microphone 7406, and the like. Note that the cellular phone 7400 is manufactured using a light-emitting device for the display portion 7402.

When the display portion 7402 of the cellular phone 7400 illustrated in FIG. 7D is touched with a finger or the like, data can be input into the cellular phone 7400. Further, operations such as making calls and composing e-mails can be performed by touching the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or composing an e-mail, a text input mode mainly for inputting text is selected for the display portion 7402 so that text displayed on a screen can be inputted. In that case, it is preferable to display a keyboard or number buttons on almost all the area of the screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touching the display portion 7402 or operating the operation buttons 7403 of the housing 7401. Alternatively, the screen modes can be switched depending on kinds of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed within a specified period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by touching the display portion 7402 with the palm or the finger, whereby personal authentication can be performed. Further, by providing a backlight or a sensing light source which emits a near-infrared light in the display portion, an image of a finger vein, a palm vein, or the like can be taken.

Figure 7E:
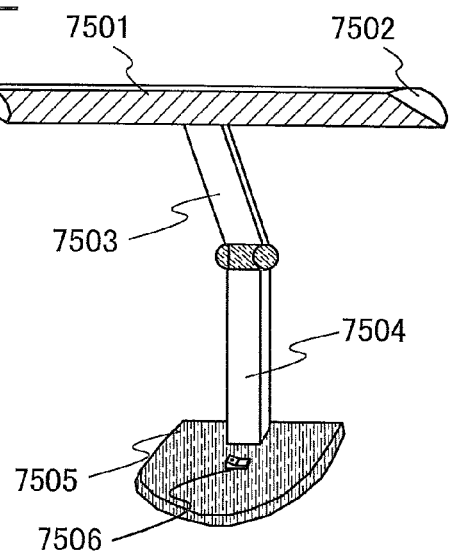

FIG. 7E illustrates a desk lamp including a lighting portion 7501, a shade 7502, an adjustable arm 7503, a support 7504, a base 7505, and a power supply 7506. The desk lamp is manufactured using a light-emitting device for the lighting portion 7501. Note that the lighting device includes a ceiling light, a wall light, and the like.

Figure 8:
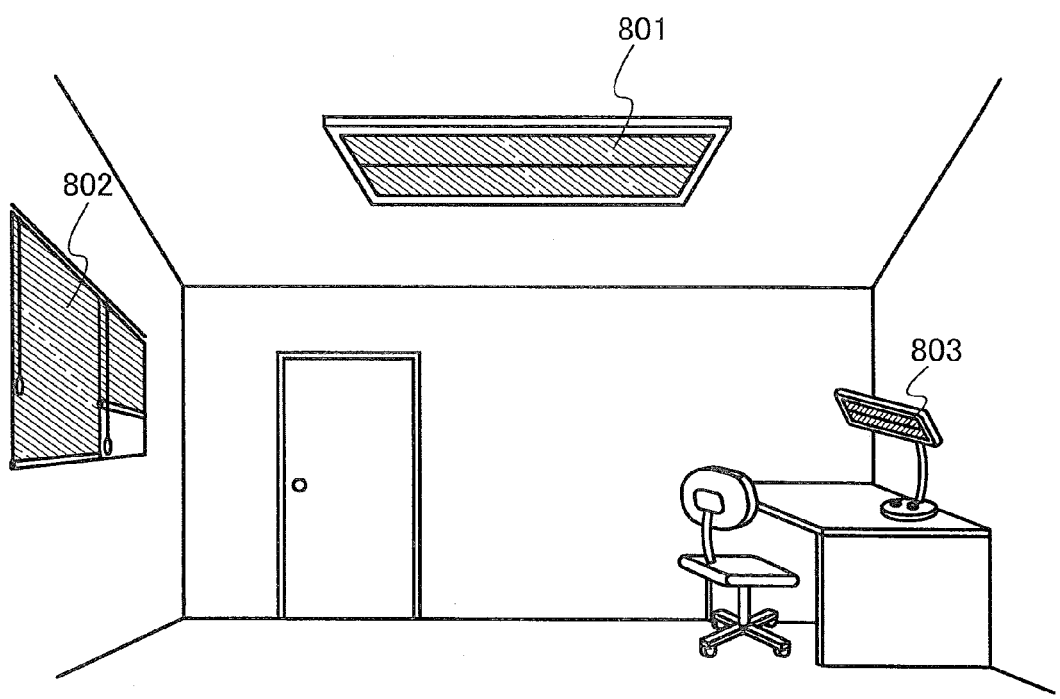
FIG. 8 is a view illustrating lighting devices.

FIG. 8 illustrates an example in which the light-emitting device is used for an indoor lighting device 801. Since the light-emitting device can also have a large area, the light-emitting device can be used as a lighting device having a large area. Alternatively, the light-emitting device can be used as a roll-type lighting device 802. Note that as illustrated in FIG. 8, a desk lamp 803 described with reference to FIG. 7E may be used together in a room provided with the indoor lighting device 801.

As described above, electronic devices and lighting devices can be obtained by application of the light-emitting device. The light-emitting device has a remarkably wide application range, and can be applied to electronic devices in various fields.

Note that the structure described in this embodiment can be combined with any of the structures described in Embodiments 1 to 6 as appropriate.

EXAMPLE 1

Synthesis Example

Example 1 shows a method of synthesizing (acetylacetonato)bis[3,5-dimethyl-2-(3-diphenylaminophenyl)pyrazinato]iridium(III) (abbreviation: [Ir(dm5dpappr)₂(acac)]), which is the organometallic complex according to one embodiment of the present invention represented by the structural formula (100) in Embodiment 1. The structure of [Ir(dm5dpappr)₂(acac)] is shown below.

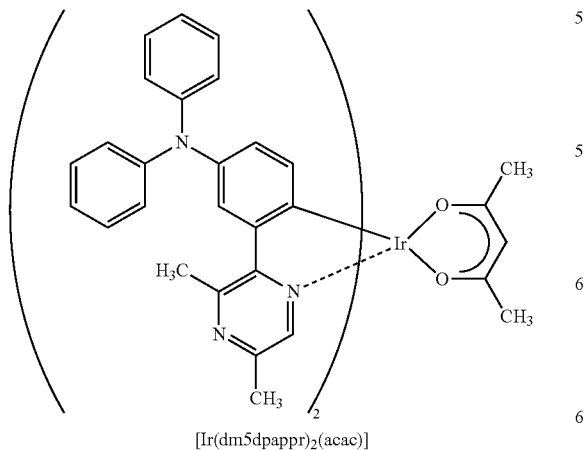

[Ir(dm5dpappr)₂(acac)]

Step 1: Synthesis of 2-(3-Diphenylaminophenyl)-1,3,2-dioxaborolane

First, 0.45 g of magnesium and 5 ml of THF were suspended, and a tiny amount of 1,2-dibromoethane was added to the obtained suspension. A mixed solution of 3.0 g of 3-bromo-N,N-diphenylaniline and 30 mL of THF was dripped to this suspension, and the mixture was stirred while being heated under reflux for 1.5 hours to cause a reaction. After the reaction, the solution which was naturally cooled to room temperature was cooled to −78° C., and 1.95 g of trimethyl borate was added thereto. The mixture was stirred while the temperature was increased to room temperature to cause a reaction. After the reaction, the solution was concentrated, and 4.8 mL of ethylene glycol and 30 mL of toluene were added to the obtained residue. The mixture was stirred while being heated under reflux for 12 hours to cause a reaction. After the reaction, the solution was filtered and the obtained filtrate was concentrated, so that a while solid was obtained (88% yield). The synthesis scheme of Step 1 is shown by (a-1).

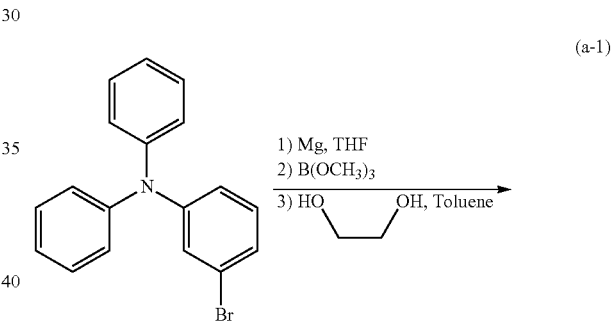

(a-1)

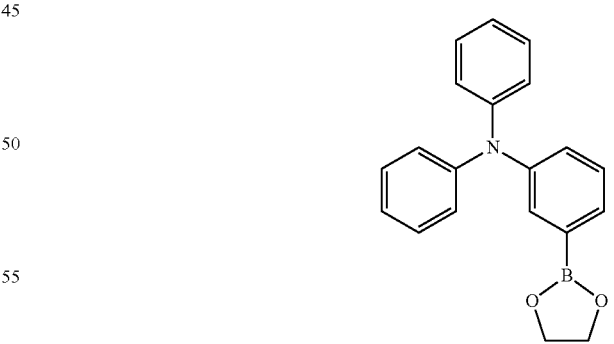

Step 2: Synthesis of 3,5-Dimethyl-2-(3-diphenylaminophenyl)pyrazine (abbreviation: Hdm5dpappr)

Next, there were put 0.39 g of 2-chloro-3,5-dimethylpyrazine, 0.87 g of 2-(3-diphenylaminophenyl)-1,3,2-dioxaborolane which was obtained in Step 1, 0.30 g of sodium carbonate, 0.013 g of bis(triphenylphosphine)palladium(II) dichloride (abbreviation: Pd(PPh₃)₂Cl₂), 10 mL of water, and 10 mL of acetonitrile in a recovery flask equipped with a reflux pipe. The air in the flask was then replaced by argon. This reaction container was heated by microwave irradiation (2.45 GHz, 100 W) for 20 minutes. After that, the reaction container was cooled to 50° C. or lower. Then, water was added to the reaction solution, and the organic layer was subjected to extraction with dichloromethane. The obtained organic layer was washed with water and dried with magnesium sulfate. After the drying, the solution was filtered. The solvent of this solution was distilled, and the obtained residue was purified by silica gel column chromatography using a mixed solvent of dichloromethane and ethyl acetate as a developing solvent, thereby obtaining the objective pyrazine derivative Hdm5dpappr (white powder, 11% yield). Note that the microwave irradiation was performed using a microwave synthesis system (Discover, produced by CEM Corporation). The synthesis scheme of Step 2 is shown by (b-1).

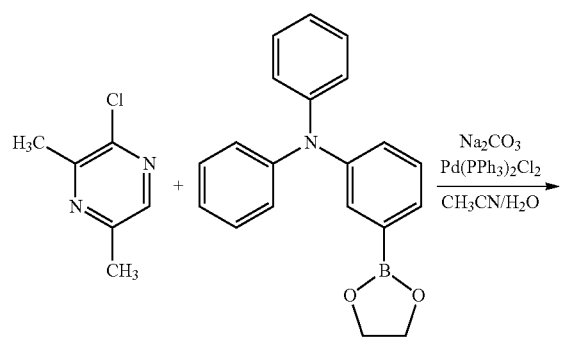

(b-1)

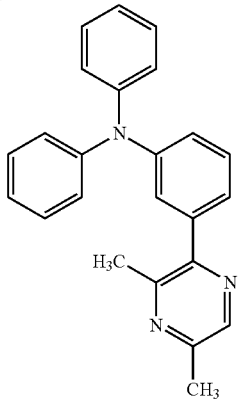

Hdm5dpappr

Step 3: Synthesis of Di-μ-chloro-bis{3,5-dimethyl-2-(3-diphenylaminophenyl)pyrazinato}iridium(III)] (abbreviation: [Ir(dm5dpappr)₂Cl]₂)

Next, there were put 3 mL of 2-ethoxyethanol, 1 mL of water, 0.11 g of Hdm5dpappr obtained in Step 2, and 0.044 g of iridium chloride hydrate (IrCl₃·H₂O) (produced by Sigma-Aldrich Corp.) in a recovery flask equipped with a reflux pipe. The air in the flask was replaced by argon. After that, the mixture was heated by microwave irradiation (2.45 GHz, 100 W) for 20 minutes. Then, the reaction container was cooled to 50° C. or lower, and the reaction solution was filtered. The obtained filtrate was washed with ethanol, so that the binuclear complex [Ir(dm5dpappr)₂Cl]₂ was obtained as red powder (53% yield). The synthesis scheme of Step 3 is shown by (c-1).

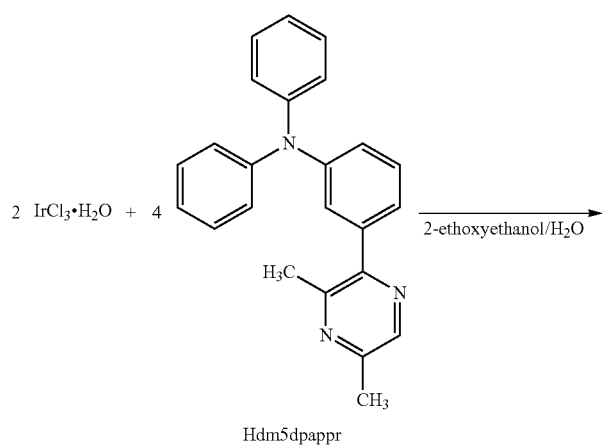

(c-1)

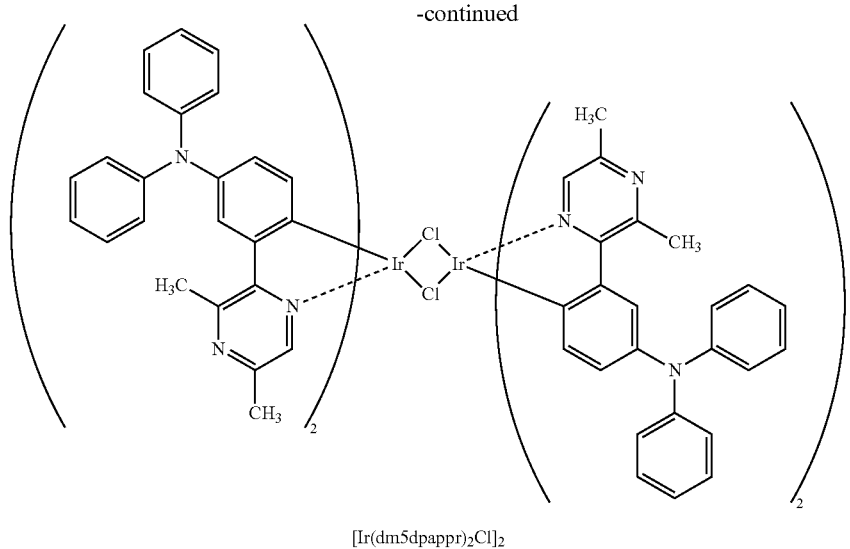

[Ir(dm5dpappr)₂Cl]₂

Step 4: Synthesis of (Acetylacetonato)bis[3,5-dimethyl-2-(3-diphenylaminophenyl)pyrazinato]iridium(III) (abbreviation: [Ir(dm5dpappr)₂(acac)])

Further, there were put 15 mL of 2-ethoxyethanol, 0.08 g of the binuclear complex [Ir(dm5dpappr)₂Cl]₂ obtained in Step 3, 0.01 mL of acetylacetone, and 0.04 g of sodium carbonate in a recovery flask equipped with a reflux pipe. The air in the flask was replaced by argon. After that, the mixture was heated by microwave irradiation (2.45 GHz, 100 VT) for 20 minutes. Then, the reaction container was cooled to 50° C. or lower, and the reaction solution was concentrated and dried. The obtained residue was dissolved in dichloromethane, and filtration was performed to remove insoluble solids. The obtained filtrate was concentrated and recrystallization with dichloromethane was performed, so that the organometallic complex [Ir(dm5dpappr)₂(acac)] according to one embodiment of the present invention was obtained as dark red powder (81% yield). The synthesis scheme of Step 4 is shown by (d-1).

(d-1)

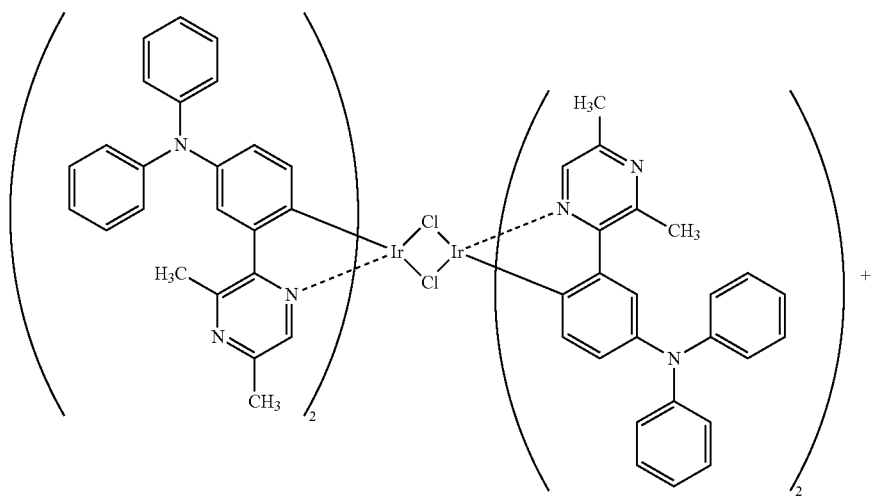

[Ir(dm5dpappr)₂Cl]₂ +

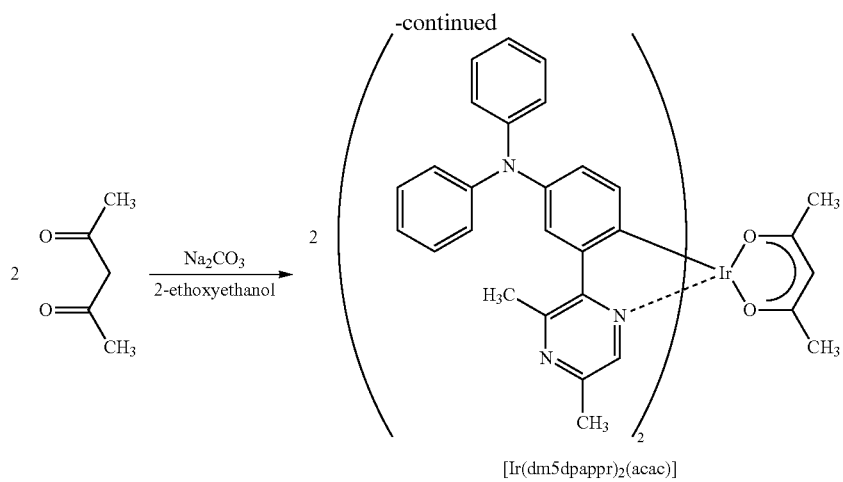

[Ir(dm5dpappr)₂(acac)]

Figure 9:
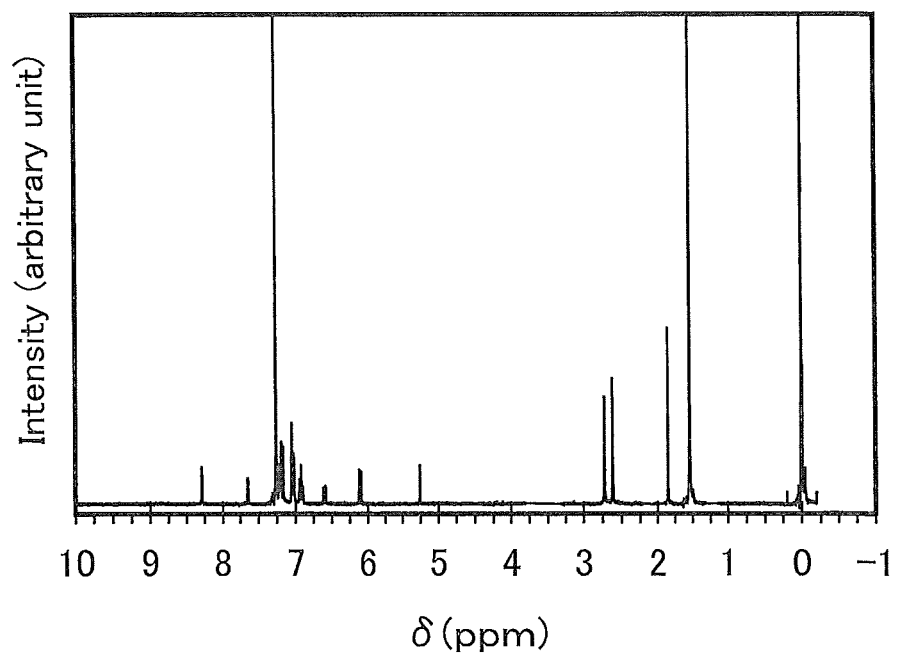
FIG. 9 shows a $^1$H-NMR chart of an organometallic complex represented by a structural formula (100).

Results of analysis of the dark red powder obtained in Step 4 by nuclear magnetic resonance spectrometry (¹H-NMR) are shown below. FIG. 9 shows the ¹H-NMR chart. According to the results, it was found that the organometallic complex [Ir(dm5dpappr)₂(acac)], one embodiment of the present invention represented by the structural formula (100), was obtained in this example.

¹H-NMR. δ (CDCl₃): 1.85 (s, 6H), 2.62 (s, 6H), 2.73 (s, 6H), 5.26 (s, 1H), 6.11 (d, 2H), 6.60 (dd, 2H), 6.92 (m, 4H), 7.05 (m, 6H), 7.19 (m, 10H), 7.65 (d, 2H), 8.29 (s, 2H).

Figure 10:
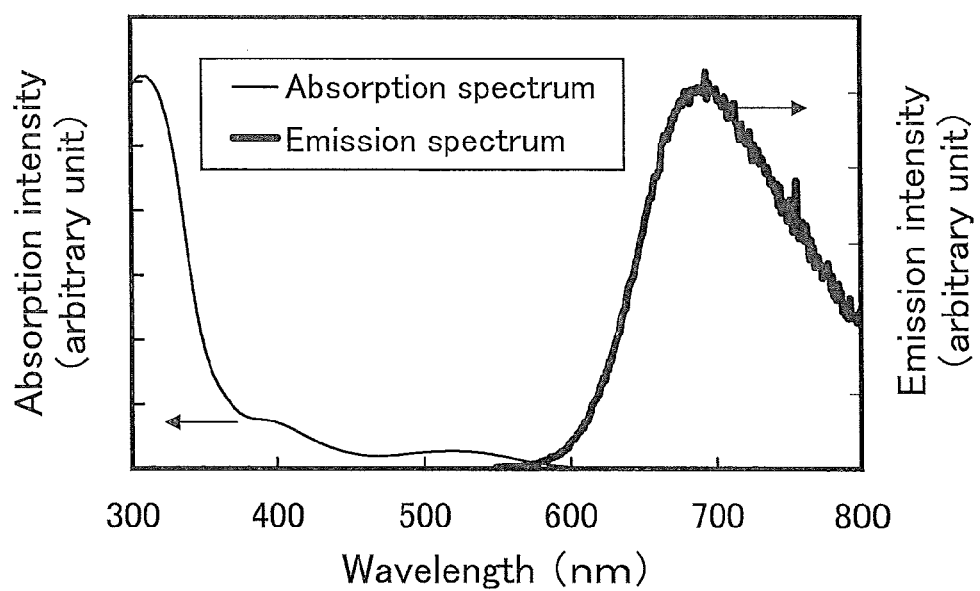
FIG. 10 shows an ultraviolet-visible absorption spectrum and an emission spectrum of the organometallic complex represented by the structural formula (100).

Next, [Ir(dm5dpappr)₂(acac)] was analyzed by ultraviolet-visible (UV-vis) absorption spectroscopy. The UV-vis spectrum was measured with an ultraviolet-visible spectrophotometer (V-550, produced by JASCO Corporation) using a dichloromethane solution (0.051 mmol/L) at room temperature. Further, an emission spectrum of [Ir(dm5dpappr)₂(acac)] was measured. The emission spectrum was measured by a fluorescence spectrophotometer (FS920, produced by Hamamatsu Photonics Corporation) using a degassed dichloromethane solution (0.31 mmol/L) at a room temperature. FIG. 10 shows the measurement results. In FIG. 10, the horizontal axis represents wavelength and the vertical axis represents absorption intensity and emission intensity.

As shown in FIG. 10, the organometallic complex [Ir(dm5dpappr)₂(acac)] which is one embodiment of the present invention has a peak of emission at 690 nm, and deep red light was observed from the dichloromethane solution.

COMPARATIVE EXAMPLE

Comparative Synthesis Example

Comparative Example shows a method of synthesizing (acetylacetonato)bis[3,5-dimethyl-2-(4-diphenylaminophenyl)pyrazinato]iridium(III) (abbreviation: [Ir(dmdpappr)₂(acac)]). The structure of [Ir(dmdpappr)₂(acac)] is shown below.

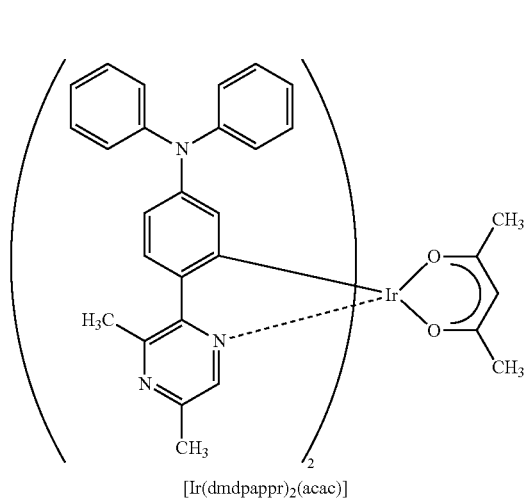

[Ir(dmdpappr)₂(acac)]

Step 1: Synthesis of 4,4,5,5-Tetramethyl-2-(4-diphenylaminophenyl)-1,3,2-dioxaborolane First, there were put 1.0 g of 4-bromotriphenylamine, 0.86 g of bis(pinacol)diborane, 1.8 g of potassium acetate, and 100 mL of N,N-dimethylformamide (abbreviation: DMF) in a 200 mL three-neck flask. The air in the flask was replaced by nitrogen. Then, 150 mg of [1,1'-bis(diphenylphosphino)ferrocene]palladium(II)dichloride dichloromethane adduct (abbreviation: PdCl₂(dppf)) was added to this mixture, and the mixture was heated and stirred under a nitrogen stream at 80° C. for 30 hours to cause a reaction. After the reaction, about 100 mL of water was added to the solution and the mixture was stirred for 30 minutes. After the stirring, this suspension was separated, and an organic layer was fractionated. The resulting aqueous layer was subjected to extraction with ethyl acetate and combined with the previously obtained organic layer, and washing was performed using water and saturated saline in this order. After the washing, anhydrate magnesium sulfate was added to the solution for drying. After the drying, the solution was gravity filtered and the resulting filtrate was concentrated to obtain a brown oily substance. This brown oily substance was dissolved in hexane and the precipitated solid was removed by filtration, thereby obtaining a filtrate. This filtrate was concentrated to obtain a pale yellow oily substance (96% yield). The synthesis scheme of Step 1 is shown by (a-2).

solution was distilled, and the obtained residue was purified by silica gel column chromatography using a mixed solvent of dichloromethane and ethyl acetate as a developing solvent, thereby obtaining the objective pyrazine derivative Hdmdpappr (white powder, 30% yield). Note that the microwave irradiation was performed using a microwave synthesis system (Discover, produced by CEM Corporation). The synthesis scheme of Step 2 is shown by (b-2).

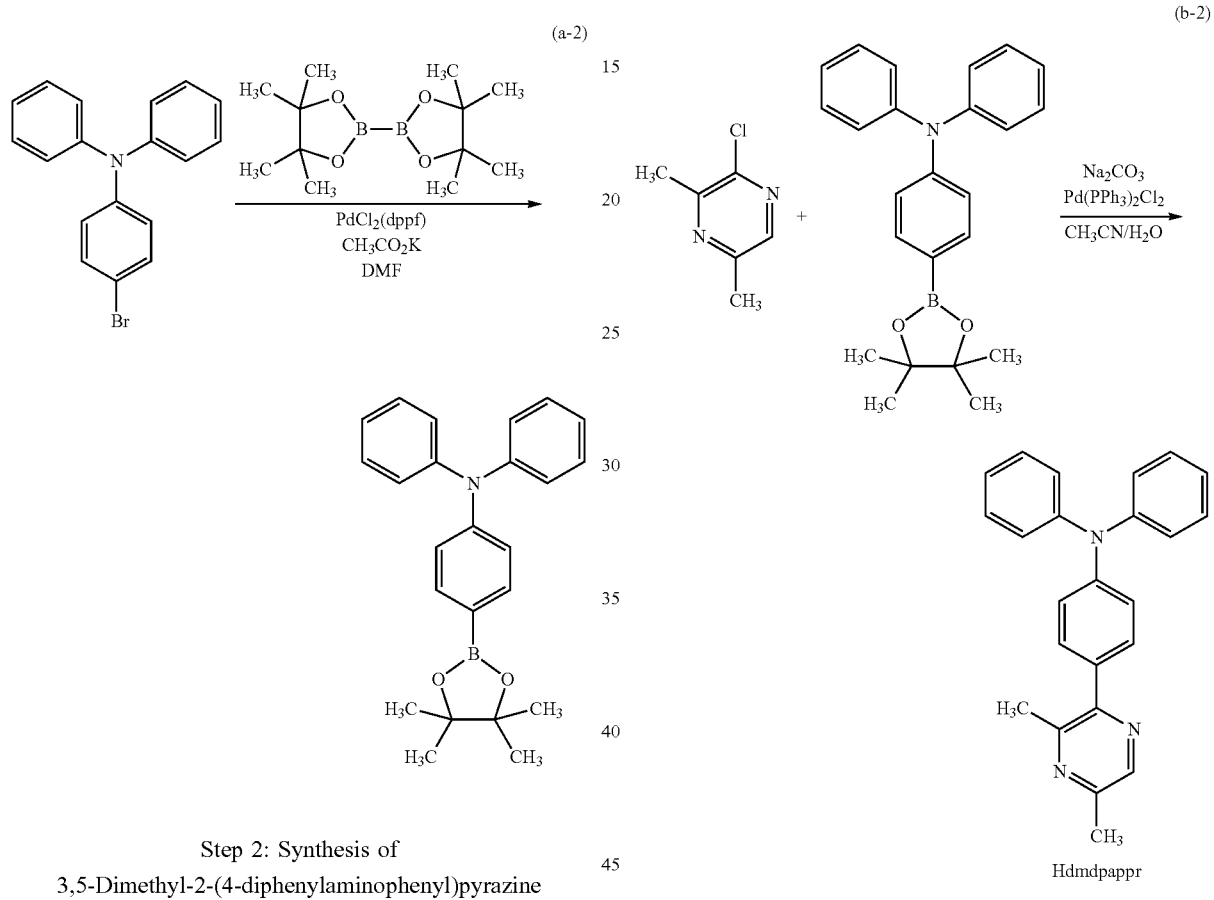

Step 2: Synthesis of 3,5-Dimethyl-2-(4-diphenylaminophenyl)pyrazine (abbreviation: Hdmdpappr)

Next, there were put 0.36 g of 2-chloro-3,5-dimethylpyrazine, 0.92 g of 4,4,5,5-tetramethyl-2-(4-diphenylaminophenyl)-1,3,2-dioxaborolane obtained in Step 1, 0.26 g of sodium carbonate, 0.011 g of bis(triphenylphosphine)palladium(II)dichloride (abbreviation: Pd(PPh$_3$)$_2$Cl$_2$), 10 mL of water, and 10 mL of acetonitrile in a recovery flask equipped with a reflux pipe. The air in the flask was replaced by argon. This reaction container was heated by microwave irradiation (2.45 GHz, 100 W) for 20 minutes. After that, the reaction container was cooled to 50° C. or lower, water was added to the reaction solution, and the organic layer was subjected to extraction with dichloromethane. The obtained organic layer was washed with water and dried with magnesium sulfate. After the drying, the solution was filtered. The solvent of this Step 3: Synthesis of Di-μ-chloro-bis[bis{3,5-dimethyl-2-(4-diphenylaminophenyl)pyrazinato}iridium (III)] (abbreviation: [Ir(dmdpappr)$_2$Cl]$_2$)

Next, there were put 6 mL of 2-ethoxyethanol, 2 mL of water, 0.26 g of Hdmdpappr obtained in Step 2, and 0.11 g of iridium chloride hydrate (IrCl$_3$.H$_2$O) (produced by Sigma-Aldrich Corp.) in a recovery flask equipped with a reflux pipe. The air in the flask was replaced by argon. After that, the mixture was heated by microwave irradiation (2.45 GHz, 100 W) for 20 minutes. Then, the reaction container was cooled to 50° C. or lower, and the reaction solution was filtered. The obtained residue was washed with ethanol, so that a binuclear complex [Ir(dmdpappr)$_2$Cl]$_2$ was obtained as ocher powder (74% yield). The synthesis scheme of Step 3 is shown in (c-2).

(c-2)

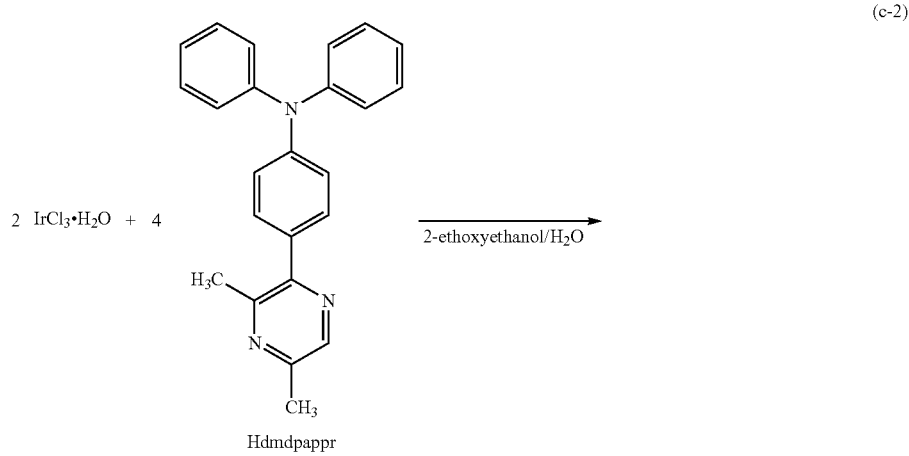

Hdmdpappr

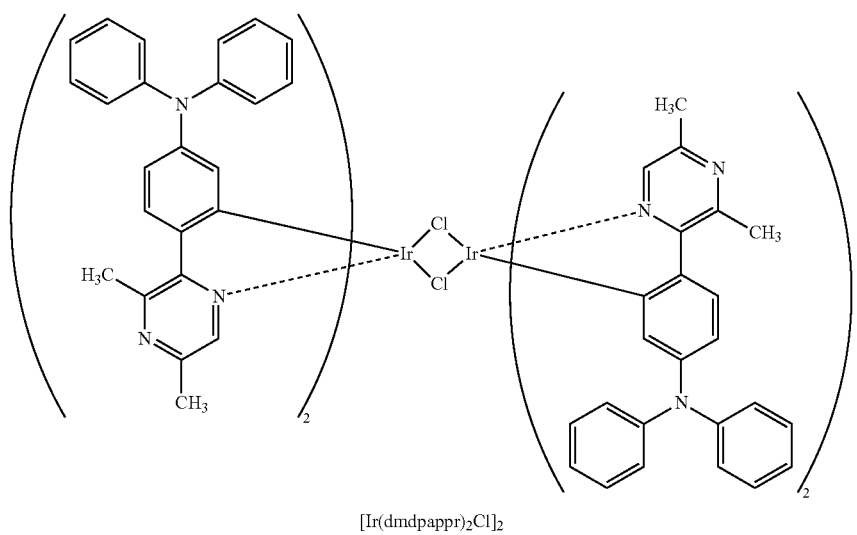

[Ir(dmdpappr)₂Cl]₂

Step 4: Synthesis of (Acetylacetonato)bis[3,5-dimethyl-2-(4-diphenylaminophenyl)pyrazinato]iridium (III) (abbreviation: [Ir(dmdpappr)₂(acac)])

Further, there were put 10 mL of 2-ethoxyethanol, 0.24 g of the binuclear complex [Ir(dmdpappr)₂Cl]₂ obtained in Step 3, 0.040 mL of acetylacetone, and 0.14 g of sodium carbonate in a recovery flask equipped with a reflux pipe. The air in the flask was replaced by argon. After that, the mixture was heated by microwave irradiation (2.45 GHz, 100 W) for 20 minutes. Then, the reaction container was cooled to 50° C. or lower, and the reaction solution was concentrated and dried. The obtained residue was dissolved in dichloromethane, and filtration was performed to remove insoluble solids. The obtained filtrate was concentrated and the residue was purified by silica gel column chromatography using ethyl acetate as a developing solvent, thereby obtaining [Ir(dmdpappr)₂(acac)] as red powder (8% yield). The synthesis scheme of Step 4 is shown by (d-2).

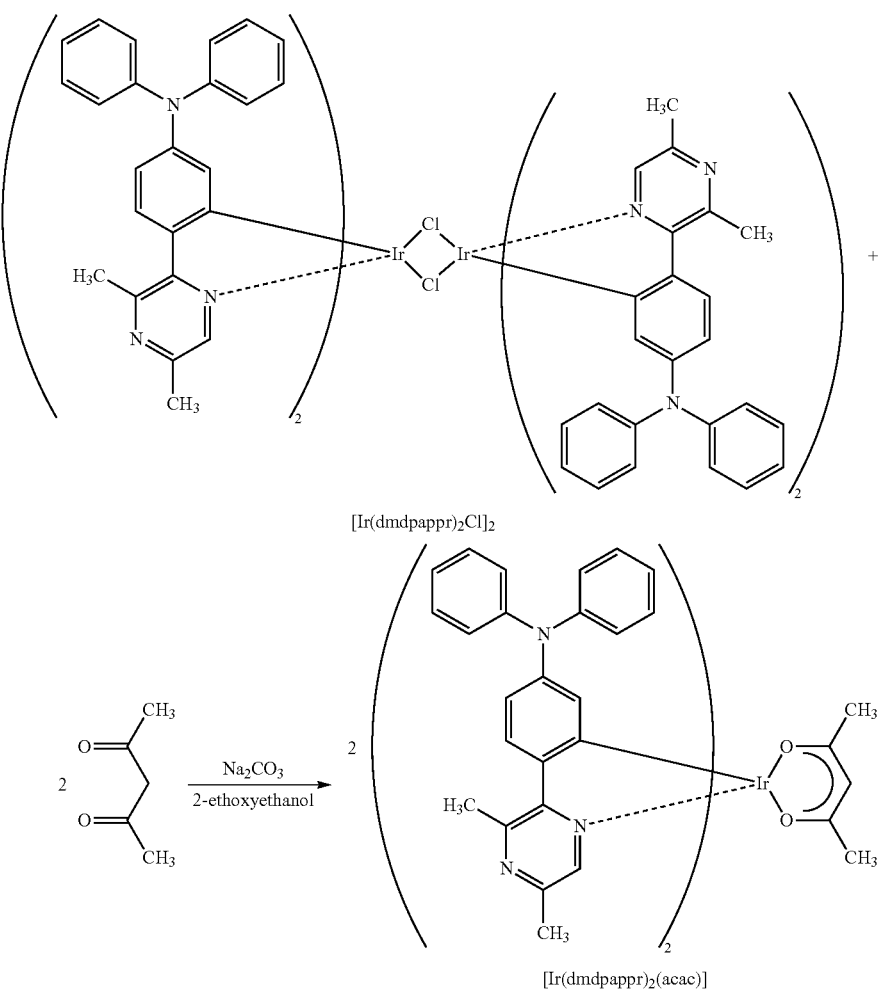

[Ir(dmdpappr)₂Cl]₂

[Ir(dmdpappr)₂(acac)]

Figure 11:
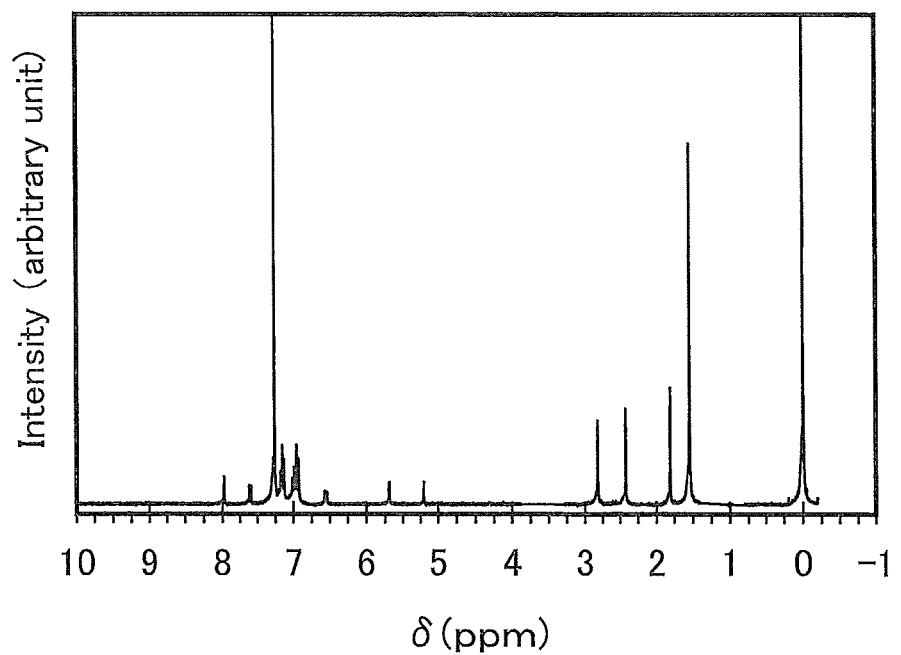
FIG. 11 shows a $^1$H-NMR chart of [Ir(dmdpappr)$_2$(acac)] synthesized in Comparative Example.

Results of analysis of the red powder obtained in Step 4 by nuclear magnetic resonance spectrometry ($^1$H-NMR) are shown below. FIG. 11 shows the $^1$H-NMR chart. According to the results, it was found that [Ir(dmdpappr)₂(acac)] was obtained.

$^1$H-NMR. δ (CDCl₃): 1.81 (s, 6H), 2.42 (s, 6H), 2.82 (s, 6H), 5.20 (s, 1H), 5.69 (d, 2H), 6.55 (dd, 2H), 6.95 (m, 12H), 7.15 (m, 8H), 7.60 (d, 2H), 7.97 (s, 2H).

Figure 12:
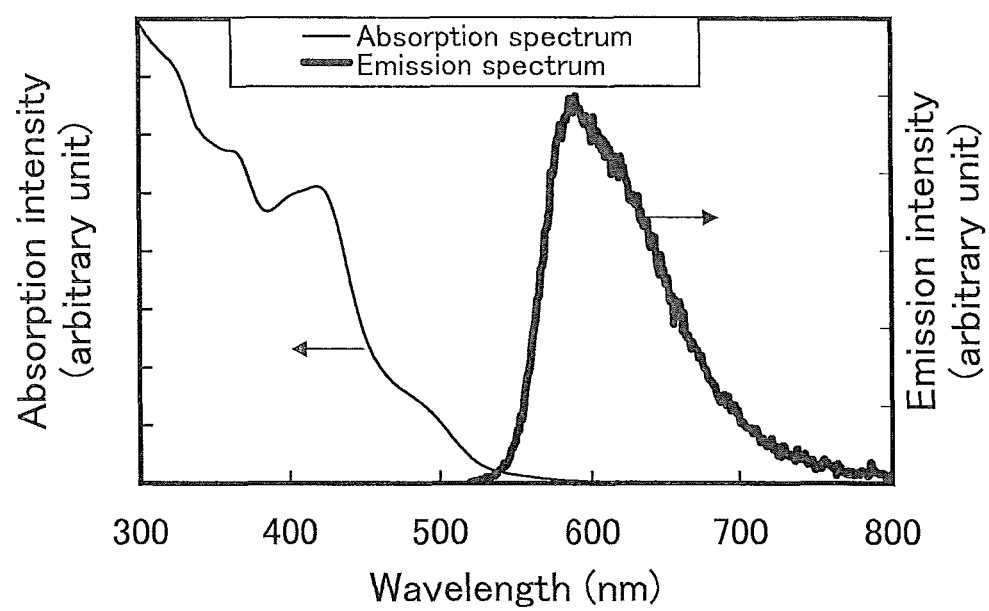
FIG. 12 shows an ultraviolet-visible absorption spectrum and an emission spectrum of [Ir(dmdpappr)$_2$(acac)] synthesized in Comparative Example.

Next, [Ir(dmdpappr)₂(acac)] was analyzed by ultraviolet-visible (UV-vis) absorption spectroscopy. The UV-vis spectrum was measured with an ultraviolet-visible spectrophotometer (V-550, produced by JASCO Corporation) using a dichloromethane solution (0.067 mmol/L) at room temperature. Further, an emission spectrum of [Ir(dmdpappr)₂(acac)] was measured. The emission spectrum was measured by a fluorescence spectrophotometer (FS920, produced by Hamamatsu Photonics Corporation) using a degassed dichloromethane solution (0.40 mmol/L) at a room temperature. FIG. 12 shows the measurement results. In FIG. 12, the horizontal axis represents wavelength and the vertical axis represents absorption intensity and emission intensity.

As shown in FIG. 12, [Ir(dmdpappr)₂(acac)] has a peak of emission at 590 nm, and orange light was observed from the dichloromethane solution.

This application is based on Japanese Patent Application serial no. 2010-287239 filed with Japan Patent Office on Dec. 24, 2010, the entire contents of which are hereby incorporated by reference.

What is claimed is:

1. A light-emitting element comprising an organometallic complex comprising a structure represented by a formula (G1),

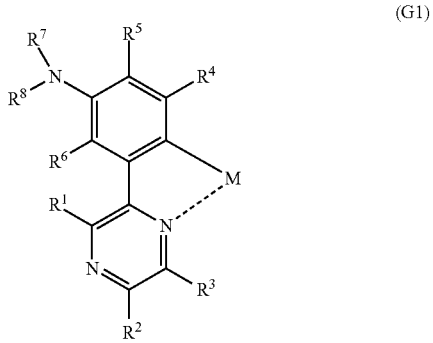

(G1)

wherein $R^1$ represents any of an alkyl group having 1 to 4 carbon atoms, an alkoxy group having 1 to 4 carbon atoms, and an alkoxycarbonyl group having 1 to 5 carbon atoms, wherein $R^2$ and $R^3$ independently represent hydrogen or an alkyl group having 1 to 4 carbon atoms, wherein $R^4$, $R^5$, and $R^6$ independently represent any of hydrogen, an alkyl group having 1 to 4 carbon atoms, an alkoxy group having 1 to 4 carbon atoms, a halogen, a trifluoromethyl group, and an aryl group having 6 to 12 carbon atoms, wherein $R^7$ and $R^8$ independently represent an alkyl group having 1 to 4 carbon atoms or an aryl group having 6 to 12 carbon atoms, and wherein M is iridium.

2. The light-emitting element according to claim 1, wherein the structure is represented by a formula (G2),

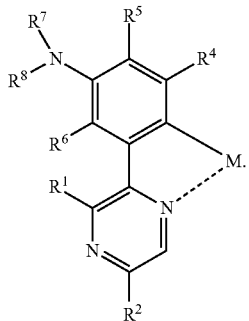
(G2)

3. The light-emitting element according to claim 1, wherein the structure is represented by a formula (G3),

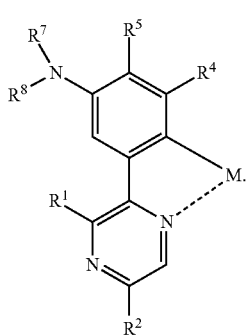
(G3)

4. An electronic device comprising a light-emitting device comprising the light-emitting element according to claim 1.

5. A lighting device comprising a light-emitting device comprising the light-emitting element according to claim 1.

6. A light-emitting element comprising an organometallic complex comprising a structure represented by a formula (G4),

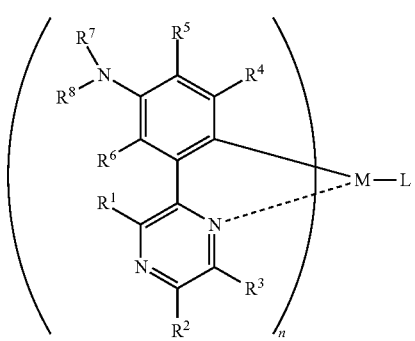
(G4)

wherein $R^1$ represents any of an alkyl group having 1 to 4 carbon atoms, an alkoxy group having 1 to 4 carbon atoms, and an alkoxycarbonyl group having 1 to 5 carbon atoms, wherein $R^2$ and $R^3$ independently represent hydrogen or an alkyl group having 1 to 4 carbon atoms, wherein $R^4$, $R^5$, and $R^6$ independently represent any of hydrogen, an alkyl group having 1 to 4 carbon atoms, an alkoxy group having 1 to 4 carbon atoms, a halogen, a trifluoromethyl group, and an aryl group having 6 to 12 carbon atoms, wherein $R^7$ and $R^8$ independently represent an alkyl group having 1 to 4 carbon atoms or an aryl group having 6 to 12 carbon atoms, wherein L represents any of formula (L1), formula (L2), formula (L3), formula (L4), formula (L5), formula (L6), formula (L7) and formula (L8):

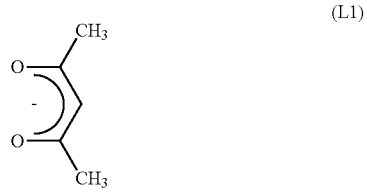
(L1)

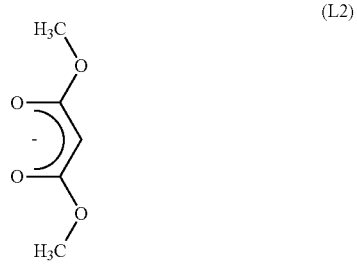
(L2)

(L3)

(L4)

(L5)

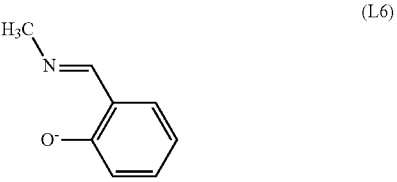
(L6)

-continued (L7)

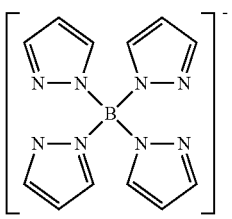

(L8)

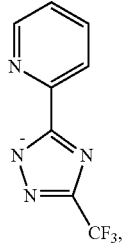

wherein M is iridium,
wherein n is 2, and
wherein the monoanionic ligand is any of a monoanionic bidentate chelate ligand having a β-diketone structure and a monoanionic bidentate chelate ligand having a carboxyl group.

7. The light-emitting element according to claim 6, wherein the structure is represented by a formula (G6), (G6)

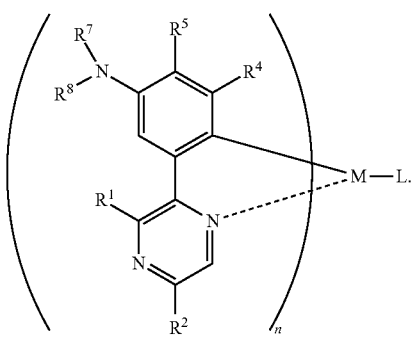

8. The light-emitting element according to claim 6, wherein the monoanionic ligand is selected from the group consisting of formula (L1) and formula (L2):

(L1)

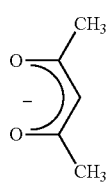

(L2)

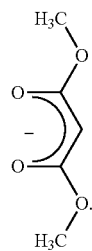

9. An electronic device comprising a light-emitting device comprising the light-emitting element according to claim 6.

10. A lighting device comprising a light-emitting device comprising the light-emitting element according to claim 6.

11. A light-emitting element comprising an organometallic complex comprising a structure represented by a formula (G4), (G4)

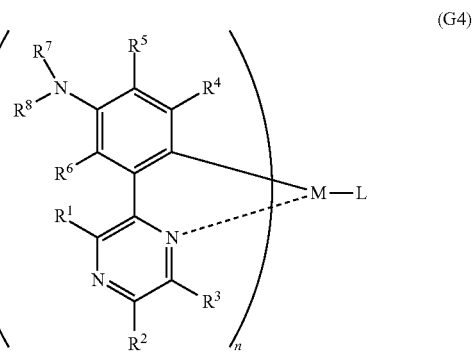

wherein $R^1$ represents any of an alkyl group having 1 to 4 carbon atoms, an alkoxy group having 1 to 4 carbon atoms, and an alkoxycarbonyl group having 1 to 5 carbon atoms,
wherein $R^2$ and $R^3$ independently represent hydrogen or an alkyl group having 1 to 4 carbon atoms,
wherein $R^4$, $R^5$, and $R^6$ independently represent any of hydrogen, an alkyl group having 1 to 4 carbon atoms, an alkoxy group having 1 to 4 carbon atoms, a halogen, a trifluoromethyl group, and an aryl group having 6 to 12 carbon atoms,
wherein $R^7$ and $R^8$ are bonded to each other through a carbon atom, an oxygen atom, a sulfur atom, or a nitrogen atom having a methyl group, to form a five-membered ring or a six-membered ring,
wherein L represents any of formula (L1), formula (L2), formula (L3), formula (L4), formula (L5), formula (L6), formula (L7) and formula (L8):

(L1)

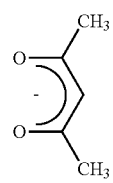

(L2)

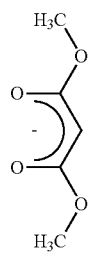

(L3)

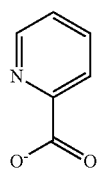

-continued

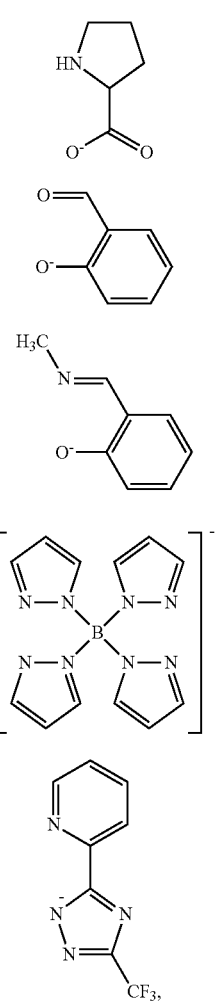

(L4)

(L5)

(L6)

(L7)

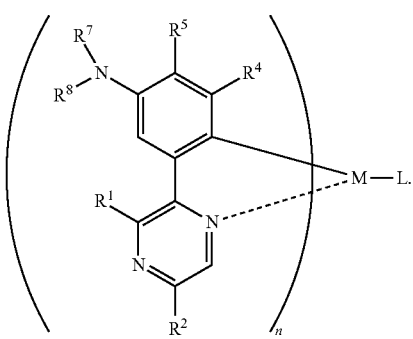

(L8)

wherein M is iridium,
wherein n is 2, and
wherein the monoanionic ligand is any of a monoanionic bidentate chelate ligand having a β-diketone structure and a monoanionic bidentate chelate ligand having a carboxyl group.

12. The light-emitting element according to claim 10, wherein the structure is represented by a formula (G6),

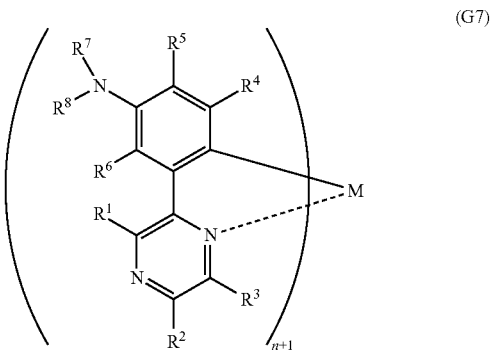

(G6)

13. The light-emitting element according to claim 11, wherein the monoanionic ligand is selected from the group consisting of formula (L1) and formula (L2):

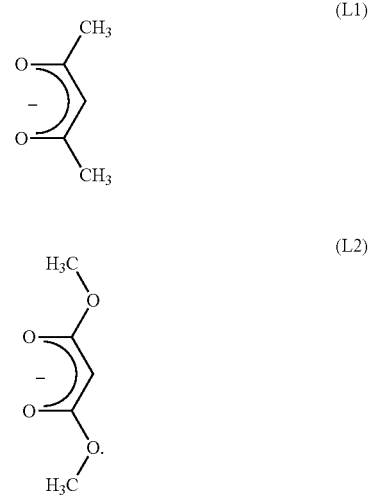

(L1)

(L2)

14. An electronic device comprising a light-emitting device comprising the light-emitting element according to claim 11.

15. A lighting device comprising a light-emitting device comprising the light-emitting element according to claim 11.

16. A light-emitting element comprising an organometallic complex comprising a structure represented by a formula (G7), (G7)

wherein $R^1$ represents any of an alkyl group having 1 to 4 carbon atoms, an alkoxy group having 1 to 4 carbon atoms, and an alkoxycarbonyl group having 1 to 5 carbon atoms, wherein $R^2$ and $R^3$ independently represent hydrogen or an alkyl group having 1 to 4 carbon atoms, wherein $R^4$, $R^5$, and $R^6$ independently represent any of hydrogen, an alkyl group having 1 to 4 carbon atoms, an alkoxy group having 1 to 4 carbon atoms, a halogen, a trifluoromethyl group, and an aryl group having 6 to 12 carbon atoms, wherein $R^7$ and $R^8$ independently represent an alkyl group having 1 to 4 carbon atoms or an aryl group having 6 to 12 carbon atoms, wherein M is iridium, and wherein n is 2.

17. The light-emitting element according to claim 16, wherein the structure is represented by a formula (G8),

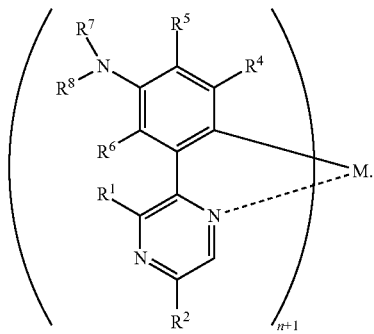

(G8)

18. The light-emitting element according to claim 16, wherein the structure is represented by a formula (G9),

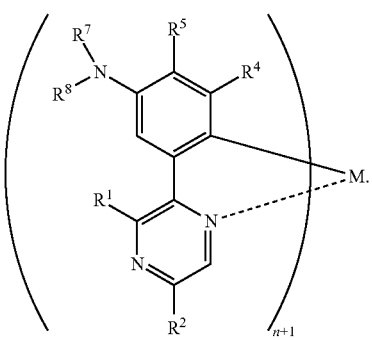

(G9)

19. An electronic device comprising a light-emitting device comprising the light-emitting element according to claim 16.

20. A lighting device comprising a light-emitting device comprising the light-emitting element according to claim 16.

* * * * *

UNITED STATES PATENT AND TRADEMARK OFFICE
CERTIFICATE OF CORRECTION

PATENT NO. : 9,508,941 B2
APPLICATION NO. : 14/286219
DATED : November 29, 2016
INVENTOR(S) : Hideko Inoue et al.

It is certified that error appears in the above-identified patent and that said Letters Patent is hereby corrected as shown below:

In the Specification

Column 38, Line 24; Change "$10^{-6}$ cm$^2$V·s" to --$10^{-6}$ cm$^2$/V·s--.

Column 39, Line 9; Change "PPy)" to --PF-Py)--.

Column 39, Lines 12 to 13; Change "10-6 cm$^2$V·s" to --10-6 cm$^2$/V·s--.

Column 41, Line 21; Change "DPVB 4," to --DPVBi, 4,--.

Column 45, Line 18; Change "py ran" to --pyran--.

Column 45, Line 61; Change "A-N in" to --A-A' in--.

Column 48, Line 65; Change "(R, G and B)" to --(R, G, and B)--.

Column 54, Line 26; Change "[ft(dm" to --[Ir(dm--.

Column 54, Line 33; Change "(IrCl$_3$.H$_2$O)" to --(IrCl$_3$·H$_2$O)--.

Column 56, Line 29; Change "100 VT)" to --100 W)--.

Column 60, Line 56; Change "(IrCl$_3$.H$_2$O)" to --(IrCl$_3$·H$_2$O)--.

In the Claims

Column 66, Lines 17 to 20, Claim 6; Change "wherein L represents any of formula (LI), formula (L2), formula (L3), formula (L4), formula (L5), formula (L6), formula (L7) and formula (L8):" to --wherein L represents a monoanionic ligand,--.

Signed and Sealed this
Sixth Day of June, 2017

Michelle K. Lee
*Director of the United States Patent and Trademark Office*

CERTIFICATE OF CORRECTION (continued)
U.S. Pat. No. 9,508,941 B2

Column 66, Lines 21 to 67, Claim 6; delete chemical formulas (L1), (L2), (L3), (L4), and (L5).

Column 67, Lines 1 to 20, Claim 6; delete chemical formulas (L7) and (L8).

Column 68, Lines 38 to 40, Claim 11; Change "wherein L represents any of formula (LI), formula (L2), formula (L3), formula (L4), formula (L5), formula (L6), formula (L7) and formula (L8):" to --wherein L represents a monoanionic ligand,--.

Column 68, Lines 43 to 66, Claim 11; delete chemical formulas (L1), (L2), and (L3).

Column 69, Lines 1 to 40, Claim 11; delete chemical formulas (L4), (L5), (L6), (L7) and (L8).

Column 69, Line 47, Claim 12; Change "claim 10," to --claim 11,--.